US005733771A

United States Patent [19]

Lewis et al.

[11] Patent Number: 5,733,771
[45] Date of Patent: Mar. 31, 1998

[54] CDNAS ENCODING MINOR AMPULLATE SPIDER SILK PROTEINS

[75] Inventors: Randolph V. Lewis; Mark Colgin, both of Laramie, Wyo.

[73] Assignee: University of Wyoming, Laramie, Wyo.

[21] Appl. No.: 209,747

[22] Filed: Mar. 14, 1994

[51] Int. Cl.$^6$ .............................. C12N 1/21; C07H 21/04; C07K 14/435
[52] U.S. Cl. ...................... 435/252.3; 536/23.5; 530/350
[58] Field of Search ........................ 435/252.3; 536/23.5

[56] References Cited

FOREIGN PATENT DOCUMENTS

| | | |
|---|---|---|
| 452925 | of 1991 | European Pat. Off. . |
| 0452925 | 10/1991 | European Pat. Off. . |
| 452925-A2 | 10/1991 | European Pat. Off. . |

OTHER PUBLICATIONS

Li, K. et al. (1993) "Cloning of type XVII collagen" *J. Biol. Chem.* 268(12):8825–8834.
Mori, Y. et al. (1991) "Primary structure and functional expression from complementary DNA of a brain calcium channel" Nature 350:398–402.
Dong, Z. et al. (1990) "Spider silk proteins" *Polymer Prepr.* (Am. Chem. Soc., Div. of Polym. Chem.) 31(1):197–198.
Lewis, Randolph V., Acc. Chem. Res., 25 (9), pp. 392–398, 1992.
Andersen, Svend O., Comp. Biochem. Physiol., 35 (3), pp. 705–711, 1970.
Work, Robert W., Text. Res. J., 46(7), pp. 485–492, 1976.
Gosline, J. M., et al, ACS Symp. Ser., 544 (Silk Polymers), pp. 328–341, 1994.
Craig, Catherine L., ACS Symp. Ser., 544 (Silk Polymers), pp. 54–66, 1994.
Vollrath, Fritz, ACS Symp. Ser., 544 (Silk Polymers), pp. 17–28, 1994.
Kaplan, D.L., et al, Biomaterials, pp. 3–53, 1991.
Hinman, Mike, et al, Results Probl. Cell Differ., 19, pp. 227–254, 1992.
Cunniff, Philip M., et al, ACS Symp. Ser., 544, pp. 234–251, 1994.
Dong Z., et al, Arch. Biochem. Biophys. 284 (1), pp. 53–57, 1991.
Hinman, Michael B., et al, J. Biol. Chem., 267 (27), pp. 19320–19324, 1992.
Protein Polymer Technologies, Discover, pp. 32–36, Mar., 1992.
Lewis, R. V., Inside R & D, May 8, 1991.
New Scientist, p. 18, Nov. 14, 1992.
Viney, Christopher, Inside R & D, Mar. 13, 1991.
Chemical & Engineering News, pp. 26–32, Jul. 16, 1990.
New Scientist, p. 39, Sep. 29, 1998.
Chemical & Engineering News, pp. 24, 25, Jul. 25, 1988.
Department of the Army, Washington, D.C., Corp. Source Codes: 000137000, 1p., 1991.
Zemlin, J.C., Collaborative Research Inc., Waltham, Mass., Corp. Source Codes: 400817, 78p., 1968.
Gosline, John M., et al, Nature (London), 309(5968), pp. 551–552, 1984.
Dong, Z., et al, Polymer Preprints, Div. of Polym. Chem., American Chemical Society, v31 n1, pp. 197–198, 1990.
Fornes, R.E., et al, Journal of Polymer Science, Polymer Physics Ed., v21 n7, pp. 1163–1172, 1983.
Xu, M., et al, Proceedings of the National Academy of Sciences, v87, pp. 7120–7124, 1990.

*Primary Examiner*—Robert A. Wax
*Assistant Examiner*—Kawai Lau
*Attorney, Agent, or Firm*—Birch, Stewart, Kolasch & Birch, LLP

[57] ABSTRACT cDNA clones encoding minor ampullate spidroin proteins (MiSP) are described. The translated amino acid sequence of the cloned cDNA shows that the MiSPs have a structure which exhibits an amino proximal nonrepetitive region, a repetitive portion and a carboxy-proximal nonrepetitive portion. The repetitive portion of the sequence is describable by a generic repeat formula. Comparison of the amino acid sequences derived from the translation with the sequences of short peptides obtained from solubilized minor ampullate spider silk suggests that the nonrepetitive portions of the protein are cleaved from the protein during secretion from the cells synthesizing the spidroins. This comparison also suggests that the minor ampullate spider silk is composed of at least three polypeptides.

19 Claims, 19 Drawing Sheets

```
            10         20         30         40         50
    *        *         *          *          *          *
ACATA CTAGG TTTGG TGCCG GAGCT GGAGC TGGTA CGTCT GTGCA GAAAT 60         70         80         90        100
    *        *         *          *          *          *
ACTTT GCACA TCACT TCTCC AATTG CTTCT CGGGT ATTTG TCAAA TGATT 110        120        130        140        150
    *        *         *          *          *          *
AGTTC TACAA CTTCT ACTGA TCATG CAGTA AGTGT TGCTA CGAGC GTTGC 160        170        180        190
    *        *         *          *          *          *
GCTGA AGTCA GCTTG GACTT GATGC AAATG CT ATG AAC AAC TTA CTA
                                      M   N   N   L   L>

200            210           220          230           240
  *       *      *      *      *      *      *      *     *
GGT GCC GTT AGT GGA TAT GTT TCG ACA CTA GGC AAC GCT ATT TCT
 G   A   V   S   G   Y   V   S   T   L   G   N   A   I   S>

250            260          270          280
   *      *      *      *      *      *      *      *     *
GAT GCT TCG GCA TAC GCA AAT GCT CTT TCT TCC GCT ATA GGA AAT
 D   A   S   A   Y   A   N   A   L   S   S   A   I   G   N>

290            300          310           320           330
  *      *      *      *      *      *      *      *      *
GTG TTA GCT AAT TCC GGT TCA ATT AGC GAA AGC ACT GCA TCT TCT
 V   L   A   N   S   G   S   I   S   E   S   T   A   S   S>

340           350          360           370
   *      *      *      *      *      *      *      *     *
GCT GCT TCC AGT GCT GCT TCT TCA GTC ACT ACA ACT TTG ACG TCT
 A   A   S   S   A   A   S   S   V   T   T   T   L   T   S>

380            390          400          410           420
  *      *      *      *      *      *      *      *      *
TAT GGA CCA GCT GTA TTT TAC GCA CCT TCT GCA TCA TCT GGA GGC
 Y   G   P   A   V   F   Y   A   P   S   A   S   S   G   G>

430           440          450          460
   *      *      *      *      *      *      *      *     *
TAT GGA GCT GGA GCT GGA GCT GTT GCT GCA GCA GGA GCT GCC GGC
 Y   G   A   G   A   G   A   V   A   A   A   G   A   A   G>

470            480          490          500           510
  *      *      *      *      *      *      *      *      *
GCT GGA GGT TAC GGA AGA GGT GCT GGA GGC TAC GGT GGA CAA GGA
 A   G   G   Y   G   R   G   A   G   G   Y   G   G   Q   G>
```

FIG. 1A

```
      520            530            540            550
       *              *              *              *       *
GGA TAT GGT GCC GGA GCC GGA GCT GGT GCT GCT GCA GCT GCT GGA
 G   Y   G   A   G   A   G   A   G   A   A   A   A   G>

560            570            580            590            600
   *              *              *      *       *              *
GCA GGA GCC GGA GGC GCT GGT GGT TAC GGT AGA GGT GCT GGT GCT
 A   G   A   G   G   A   G   G   Y   G   R   G   A   G   A>

610            620            630            640
       *              *       *              *              *
GGA GCT GGT GCG GCT GCT GGG GCA GGT GCA GGC GCC GGT GGT GCT
 G   A   G   A   A   A   G   A   G   A   G   A   G   G   A>

650            660            670            680            690
   *              *              *              *              *
GGA TAT GGT GGA CAA GGC GGA TAT GGT GCC GGA GCA GGA GCT GGT
 G   Y   G   G   Q   G   G   Y   G   A   G   A   G   A   G>

700            710            720            730
       *              *              *              *       *
GCG GCT GCT GCT GCT GGT GCA GGA GCA GGA GGT GCT GGC GGT TAC
 A   A   A   A   A   G   A   G   A   G   G   A   G   G   Y>

740            750            760            770            780
   *              *              *              *              *
GGT AGA GGT GCT GGT GCT GGA GCA GGA GCC GCT GCG GGT GCT GGA
 G   R   G   A   G   A   G   A   G   A   A   A   G   A   G>

790            800            810            820
       *              *              *              *       *
GCT GGA GGC TAC GGT GGT CAA GGT GGG TAC GGT GCC GGA GCA GGA
 A   G   G   Y   G   G   Q   G   G   Y   G   A   G   A   G>

830            840            850            860            870
   *              *              *              *              *
GCT GGT GCG GCT GCT GCT GCT GCT GGA GCA GGA TCT GGA GGC GCT
 A   G   A   A   A   A   A   A   G   A   G   S   G   G   A>

880            890            900            910
       *              *              *              *       *
GGC GGT TAC GGT AGA GGT GCT GGT GCT GGA GCT GGA GCC GCT GCA
 G   G   Y   G   R   G   A   G   A   G   A   G   A   A   A>

920            930            940            950            960
   *              *              *              *              *
GGT GCA GGA GCA GGA GCT GGA AGC TAC GGT GGT CAA GGA TAC GGT
 G   A   G   A   G   A   G   S   Y   G   G   Q   G   Y   G>
```

FIG. 1B

```
            970           980           990          1000
        *     *       *     *       *     *       *     *       *
       GCC GGA GCA GGA GCT GGT GCT GCT GCA GCT GCA NNN NNN NNN NNN
        A   G   A   G   A   G   A   A   A   A   A 1010          1020          1030          1040
    *     *       *     *       *     *       *     *       *
   NNN NNN NNN NNN NNN NNN NNN NNN NNN NNN GGT GCA GGT GCA
                                            G   A   G   A>

1050          1060          1070          1080          1090
 *     *       *     *       *     *       *     *       *
GGT GCT GGA TAT GGT GGA CAA GGC GGA TAT GGT GCC GGA GCA GGA
 G   A   G   Y   G   G   Q   G   G   Y   G   A   G   A   G>

1100          1110          1120          1130
        *     *       *     *       *     *       *     *       *
       GCT GGT GCG GCT GCT GCT GCT GGT GCA GGA GCT GGA GGT GCT GGT
        A   G   A   A   A   A   A   G   A   G   A   G   G   A   G>

1140          1150          1160          1170          1180
 *     *       *     *       *     *       *     *       *
GGT TAC GGT AGA GGT GCT GGT GCT GGA GCT GGA GCC GCT GCA GGT
 G   Y   G   R   G   A   G   A   G   A   G   A   A   A   G>

1190          1200          1210          1220
        *     *       *     *       *     *       *     *       *
       GCA GGA GCA GGA GCT GGA GGC TAC GGT GGT CAA AGT GGA TAC GGT
        A   G   A   G   A   G   G   Y   G   G   Q   S   G   Y   G>

1230          1240          1250          1260          1270
 *     *       *     *       *     *       *     *       *
GCC GGA GCA GGA GCT GCT GCA GCT GCT GGA GCA GGA GCT GGA GGC
 A   G   A   G   A   A   A   A   A   G   A   G   A   G   G>

1280          1290          1300          1310
        *     *       *     *       *     *       *     *       *
       GCT GGT GGT TAC GGT GA  GGT GCT GGT GCT GGA GCA GGA GCC GCT
        A   G   G   Y   G   R   G   A   G   A   G   A   G   A   A>

1320          1330          1340          1350          1360
 *     *       *     *       *     *       *     *       *
GCG GGT GCT GGA GCA GGA GCC GCT GCG GGT GCA GGA GCT GGA GGC
 A   G   A   G   A   G   A   A   A   G   A   G   A   G   G>

1370          1380          1390          1400
        *     *       *     *       *     *       *     *       *
       TAC GGT GGT CAA GGT GGG TAC GGT GCC GGT GCA GGA GCT GGT GCG
        Y   G   G   Q   G   G   Y   G   A   G   A   G   A   G   A>
```

FIG. 1C

```
      1410         1420         1430         1440         1450
   *      *     *      *     *      *     *      *     *      *
   GCT  GCT  GCT  GCT  GGA  GCA  GGA  GCT  GGA  GGC  GCT  GGT  GGT  TAC  GGT
    A    A    A    A    G    A    G    A    G    G    A    G    G    Y    G>

1460         1470         1480         1490
       *      *     *      *     *      *     *      *     *
   AGA  GGT  GCT  GGT  GCT  GGA  GCT  GGA  GCT  GCT  GCA  GGC  GCA  GGA  GCT
    R    G    A    G    A    G    A    G    A    A    A    G    A    G    A>

1500         1510         1520         1530         1540
   *      *     *      *     *      *     *      *     *
   GGA  GGC  TAC  GGT  GGT  CAA  GGT  GGA  TAC  GGT  GCC  GGA  GCA  GGA  GCT
    G    G    Y    G    G    Q    G    G    Y    G    A    G    A    G    A>

1550         1560         1570         1580
       *      *     *      *     *      *     *      *     *
   GGT  GCT  GCT  GCA  GCT  GCT  GCA  ACA  GGA  GCC  GGA  GGC  GCT  GGT  GGT
    G    A    A    A    A    A    A    T    G    A    G    G    A    G    G>

1590         1600         1610         1620         1630
   *      *     *      *     *      *     *      *     *
   TAC  GGT  AGA  GGT  GCT  GGT  GCT  GGA  GCT  GGT  GCC  GCT  GCT  GGG  GCA
    Y    G    R    G    A    G    A    G    A    G    A    A    A    G    A>

1640         1650         1660         1670
       *      *     *      *     *      *     *      *     *
   GGT  GCA  GGC  ACC  GGT  GGT  GCT  GGA  TAT  GGT  GGA  CAA  GGC  GGT  TAT
    G    A    G    T    G    G    A    G    Y    G    G    Q    G    G    Y>

1680         1690         1700         1710         1720
   *      *     *      *     *      *     *      *     *
   GGT  GCC  GGA  GCA  GGA  GCT  GGT  GCG  GCT  GCT  GCT  GCT  GGT  GCA  GGA
    G    A    G    A    G    A    G    A    A    A    A    G    A    G>

1730         1740         1750         1760
       *      *     *      *     *      *     *      *     *
   GCA  GGA  GGT  GCT  GGT  TAC  GGT  AGA  GGT  GCT  GGT  GCT  GGA  GCT  GGA
    A    G    G    A    G    Y    G    R    G    A    G    A    G    A    G>

1770         1780         1790         1800         1810
   *      *     *      *     *      *     *      *     *
   GCT  GCT  GCA  GGT  GCT  GGA  GCT  GGA  GCC  GCT  GCA  GGT  GCA  GGA  GCA
    A    A    A    G    A    G    A    G    A    A    A    G    A    G    A>

1820         1830         1840         1850
       *      *     *      *     *      *     *      *     *
   GGA  GCT  GGA  GGC  TAC  GGT  GGT  CAG  GGT  GGA  TAC  GGT  GCC  GGA  GCA
    G    A    G    G    Y    G    G    Q    G    G    Y    G    A    G    A>
```

FIG. 1D

```
      1860            1870           1880            1890           1900
        *              *              *               *              *
                *              *        *,     *              *
      AGA GCT GGT GCT GCG GCA GCT GCT GGA GCA GGA GCT GGA GGC GCT
       R   A   G   A   A   A   A   A   G   A   G   A   G   G   A>

1910           1920           1930           1940
        *      *       *      *      *       *      *      *       *
      GCG GGT TAC AGT AGA GGT GGT CGT GCA GGA GCC GCT GGT GCT GGA
       A   G   Y   S   R   G   G   R   A   G   A   A   G   A   G>

1950           1960           1970           1980           1990
        *      *       *      *      *       *      *      *       *
      GCT GGA GCC GCT GCA GGT GCA GGA GCA GGA GCT GGA GGC TAC GGT
       A   G   A   A   G   A   G   A   G   A   G   G   Y   G>

2000           2010           2020           2030
        *              *      *       *      *      *       *      *
      GGT CAA GGT GGA TAC GGT GCC GGA GCA GGA GCT GGT GCT GCT GCA
       G   Q   G   G   Y   G   A   G   A   G   A   G   A   A   A>

2040           2050           2060           2070           2080
        *      *       *      *      *       *      *      *       *
      GCT GCT GGT GCA GGA TCC GGA GGC GCT GGT GGT TAC GGT AGA GGT
       A   A   G   A   G   S   G   G   A   G   G   Y   G   R   G>

2090           2100           2110           2120
        *      *       *      *      *       *      *      *       *
      GCT GGT GCT GGA GCC GCT GCA GGA GCT GGA GCC GCT GCA GGT GCT
       A   G   A   G   A   A   G   A   G   A   A   G   A>

2130           2140           2150           2160           2170
        *      *       *      *      *       *      *      *       *
      GGA GCA GGA GCT GGA GGC TAC GGT GGT CAA GGT GGA TAC GGT GCC
       G   A   G   A   G   G   Y   G   G   Q   G   G   Y   G   A>

2180           2190           2200           2210
        *      *       *      *      *       *      *      *       *
      GGA GCA GGA GCT GCT GCA GCT GCT GGA GCA GGA GCC GGA CGT GGA
       G   A   G   A   A   A   A   A   G   A   G   A   G   R   G>

2220           2230           2240           2250           2260
        *      *       *      *      *       *      *      *       *
      GGT TAC GGA AGA GGT GCT GGT GCT GGA GGC TAC GGT GGA CAA GGA
       G   Y   G   R   G   A   G   A   G   G   Y   G   G   Q   G>

2270           2280           2290           2300
        *      *       *      *      *       *      *      *       *
      GGA TAT GGT GCC GGA GCT GGA GCC GGT GCT GCT GCA GCT GCT GGA
       G   Y   G   A   G   A   G   A   G   A   A   A   A   A   G>
```

FIG. 1E

```
     2310           2320           2330           2340           2350
  *         *              *         *              *         *         *
GCG GGA GCC GGA GGC TAT GGC GAC AAG GAG ATA GCC TGC TGG AGC
 A   G   A   G   G   Y   G   D   K   E   I   A   C   W   S>

2360           2370           2380           2390
  *         *              *         *              *         *         *
AGG TGT AGA TAC ACT GTT GCC TCC ACA ACA TCT CGT TTG AGT TCG
 R   C   R   Y   T   V   A   S   T   T   S   R   L   S   S>

2400           2410           2420           2430           2440
  *         *              *         *              *         *         *
GCC GAA GCA TCT TCT AGG ATA TCG TCG GCG GCT TCC ACT TTA GTA
 A   E   A   S   S   R   I   S   S   A   A   S   T   L   V>

2450           2460           2470           2480
  *         *              *         *              *         *         *
TCT GGA GGT TAC TTG AAT ACA GCA GCT CTG CCA TCG GTT ATT TCG
 S   G   G   Y   L   N   T   A   A   L   P   S   V   I   S>

2490           2500           2510           2520           2530
  *         *              *         *              *         *         *
GAT CTT TTT GCC CAA GTT GGT GCA TCT TCT CCG GTG ATC AGA CAG
 D   L   F   A   Q   V   G   A   S   S   P   V   I   R   Q>

2540           2550           2560           2570
  *         *              *         *              *         *         *
CGA AGT TTG ATC CAA GTT TTG TTG GAA ATT GTT TCT TCT CTT ATC
 R   S   L   I   Q   V   L   L   E   I   V   S   S   L   I>

2580           2590           2600           2610           2620
  *         *              *         *              *         *         *
CAT ATT CTC AGT TCT TCT AGC GTA GGA CAA GTC GAT TTC AGT TCG
 H   I   L   S   S   S   S   V   G   Q   V   D   F   S   S>

2630           2640           2650           2660
  *         *              *         *              *         *         *
GTT GGG TCG TCT GCT GCA GCT GTT GGT CAA TCC ATG CAA GTT GTA
 V   G   S   S   A   A   A   V   G   Q   S   M   Q   V   V>

2670           2680           2690           2700           2710
  *         *              *         *              *         *         *
ATG GGC TAA ACAT GATGG TTCTC TCAAT TATGT ATTCT TTAAT TACCG
 M   G   *>

2720           2730           2740           2750           2760
  *         *              *         *              *         *         *
CTAAG GTAGC AAAAT ATTGT AAAGT AAAGT TTTCT TACAA AATAA AAATT 2770           2780           2790
  *         *              *         *         *
CTTTT CTGCA AAAAA AAAAA AAAAA AA
```

FIG. 1F

```
         10             20             30             40
   *      *      *      *      *      *      *      *      *
  TCT    TAT    GGA    CCA    TCC    GTA    TTT    TAC    ACT    CCT    ACT    TCA    GCT    GGA    AGC
   S      Y      G      P      S      V      F      Y      T      P      T      S      A      G      S>

50             60             70             80             90
   *      *      *      *      *      *      *      *      *
  TAT    GGT    GCA    GGG    GCC    GGA    GGT    TTT    GGA    GCT    GGA    GCC    TCT    GCT    GGT
   Y      G      A      G      A      G      G      F      G      A      G      A      S      A      G>

100            110            120            130
   *      *      *      *      *      *      *      *      *
  GTC    GGA    GCC    GGA    GCT    GGT    ACT    GTA    GCA    GGA    TAT    GGT    GGA    CAA    GGA
   V      G      A      G      A      G      T      V      A      G      Y      G      G      Q      G>

140            150            160            170            180
   *      *      *      *      *      *      *      *      *
  GGA    TAT    GGT    GCC    GGA    AGC    GCT    GGA    GGT    TAT    GGA    AGA    GGT    ACT    GGA
   G      Y      G      A      G      S      A      G      G      Y      G      R      G      T      G>

190            200            210            220
   *      *      *      *      *      *      *      *      *
  GCT    GGA    GCC    GCT    GCT    GGT    GCC    GGA    GCA    GGA    GCC    ACT    GCT    GGT    GCC
   A      G      A      A      A      G      A      G      A      G      A      T      A      G      A>

230            240            250            260            270
   *      *      *      *      *      *      *      *      *
  GGA    GCA    GGA    GCC    GCT    GCT    GGT    GCC    GGA    GCA    GGA    GCA    GGT    AAT    TCA
   G      A      G      A      A      A      G      A      G      A      G      A      G      N      S>

280            290            300
   *      *      *      *      *      *      *
  GGA    GGA    TAT    AGT    GCC    GGA    GTA    GGA    GTT    GGT    GCT    GCA    GCT
   G      G      Y      S      A      G      V      G      V      G      A      A      A>
```

FIG. 2A

```
           10          20              30          40
    *       *      *    *       *       *       *    *
CT GCA GCT GCT GGA GGA GGT GCC GGA ACT GTT GGA GGT TAC GGA
    A   A   A   G   G   G   A   G   T   V   G   G   Y   G>

50          60          70          80
 *      *      *    *       *    *       *    *       *
AGA GGT GCT GGT GTA GGA GCA GGT GCC GCT GCT GGT TTT GCG GCA
 R   G   A   G   V   G   A   G   A   A   A   G   F   A   A>

90          100         110         120         130
  *      *       *       *     *       *       *    *       *
GGA GCT GGT GGT GCT GGA GGC TAC AGA AGA GAT GGA GGA TAC GGT
 G   A   G   G   A   G   G   Y   R   R   D   G   G   Y   G>

140         150         160
  *      *      *      *    *       *      *
GCT GGA GCA GGA GCT GGA GCT GCT GCA GCT G
 A   G   A   G   A   G   A   A   A   A   X>
```

FIG. 2B

```
              10            20            30            40
         *    *    *    *    *    *    *    *    *
GGT GCA GGA GGC TAT GGA AGA GGT GCT GGA GCT GGA GCT GCT GCA
 G   A   G   G   Y   G   R   G   A   G   A   G   A   A   A>

50            60            70            80            90
         *    *    *    *    *    *    *    *    *
GTC GCA GGT GCA GAT GCT GGT GGC TAT GGA AGA AAT TAT GGT GCT
 V   A   G   A   D   A   G   G   Y   G   R   N   Y   G   A>

100           110           120           130
         *    *    *    *    *    *    *    *    *
GGA ACC ACT GCT TAT GCA GGA GCC AGA GCC GGT GGT GCT GGA GGC
 G   T   T   A   Y   A   G   A   R   A   G   G   A   G   G>

140           150           160           170           180
         *    *    *    *    *    *    *    *    *
TAT GGC GGA CAA GGA GGA TAT TCT TCT GGA GCC GGT GCT GCT GCA
 Y   G   G   Q   G   G   Y   S   S   G   A   G   A   A   A>

190           200           210           220
         *    *    *    *    *    *    *    *    *
GCT TCT GGA GCA GGA GCC GAT ATC ACT AGT GGA TAC GGA AGA GGT
 A   S   G   A   G   A   D   I   T   S   G   Y   G   R   G>

230           240           250           260           270
         *    *    *    *    *    *    *    *    *
GTT GGT GCT GGA GCT GGA GCA GAA ACT ATA GGT GCT GGA GGC TAT
 V   G   A   G   A   G   A   E   T   I   G   A   G   G   Y>

280           290           300           310
         *    *    *    *    *    *    *    *    *
GGA GGT GGG GCT GGA TCA GGA GCA CGT GCG GCT TCA GCA TCC GGA
 G   G   G   A   G   S   G   A   R   A   A   S   A   S   G>

320           330           340           350           360
         *    *    *    *    *    *    *    *    *
GCT GGT ACT GGA TAT GGT TCG TCT GGA GGT TAT AAC GTA GGT ACC
 A   G   T   G   Y   G   S   S   G   G   Y   N   V   G   T>

370           380           390           400
         *    *    *    *    *    *    *    *    *
GGA ATA AGT ACT TCT TCT GGC GCT GCA TCT AGC TAC TCT GTT TCT
 G   I   S   T   S   S   G   A   A   S   S   Y   S   V   S>

410           420           430           440           450
         *    *    *    *    *    *    *    *    *
GCT GGA GGT TAT GCT TCA ACA GGT GTT GGT ATT GGA TCC ACT GTT
 A   G   G   Y   A   S   T   G   V   G   I   G   S   T   V>
```

FIG. 2C

```
              460           470           480           490
       *    *    *    *    *    *    *    *    *    *
     ACA  TCC  ACA  ACA  TCT  CGT  TTG  AGT  TCT  GCT  GAA  GCA  TGT  TCT  AGA
      T    S    T    T    S    R    L    S    S    A    E    A    C    S    R>

500           510           520           530           540
       *    *    *    *    *    *    *    *    *    *
     ATA  TCT  GCT  GCG  GCT  TCC  ACT  TTA  GTA  TCT  GGA  TCC  TTG  AAT  ACT
      I    S    A    A    A    S    T    L    V    S    G    S    L    N    T>

550           560           570           580
       *    *    *    *    *    *    *    *    *    *
     GCA  GCT  TTA  CCA  TCT  GTA  ATT  TCG  GAT  CTT  TTT  GCC  CAA  GTT  AGT
      A    A    L    P    S    V    I    S    D    L    F    A    Q    V    S>

590           600           610           620           630
       *    *    *    *    *    *    *    *    *    *
     GCA  TCA  TCA  CCC  GGG  GTA  TCA  GGT  AAC  GAA  GTT  TTG  ATT  CAA  GTT
      A    S    S    P    G    V    S    G    N    E    V    L    I    Q    V>

640           650           660           670
       *    *    *    *    *    *    *    *    *    *
     TTG  TTG  GAA  ATT  GTT  TCT  TCT  CTT  ATC  CAT  ATT  CTT  AGT  TCT  TCT
      L    L    E    I    V    S    S    L    I    H    I    L    S    S    S>

680           690           700           710           720
       *    *    *    *    *    *    *    *    *    *
     AGT  GTA  GGG  CAA  GTA  GAT  TTC  AGT  TCT  GTT  GGT  TCA  TCT  GCT  GCA
      S    V    G    Q    V    D    F    S    S    V    G    S    S    A    A>

730           740           750           760
       *    *    *    *    *    *    *    *    *    *
     GCC  GTT  GGT  CAA  TCC  ATG  CAA  GTT  GTA  ATG  GGT  TAA  AACA AAATG
      A    V    G    Q    S    M    Q    V    V    M    G    *>

770           780           790           800           810
       *    *    *    *    *    *    *    *    *    *
     GCTCT CTCTC TGTTA TATGC ATTCT GTAAT TTCTT CTAAA CTATT AAAAT 820           830           840           850           860
       *    *    *    *    *    *    *    *    *    *
     AATGT AATAA TTTCC TGCAT AAATA AAAAT ATTTT TCTGC AAAAA AAAAA

870
       *
     AAAAA
```

FIG. 2D

```
            10           20           30           40
     *       *    *       *    *       *    *       *    *
GCT GGA GCT GCT GCT GGT GCT GGA GGC TAT GAC GGA CAA GGA GGA TAT
 A   G   A   A   A   G   A   G   G   Y   D   G   Q   G   G   Y>

50           60           70           80           90
  *    *       *    *       *    *       *    *       *    *
GGT GCT GGA GCA GGA GCT GCT GCA GCT GCT GGA GCA GGA GCC GGA AGC
 G   A   G   A   G   A   A   A   A   A   G   A   G   A   G   S>

100          110          120          130          140
  *    *       *    *       *    *       *    *       *
GTT GGA GGT TAT GGA ACA GGT GCT GTA GCT GGA TCT GGA ACA GCT GCT
 V   G   G   Y   G   T   G   A   V   A   G   S   G   T   A   A>

150          160
  *    *       *    *       *
GGT GCA GGA GCC AGA GCT GGT
 G   A   G   A   R   A   G>
```

FIG. 3A

```
         10          20          30          40
    *     *     *     *     *     *     *     *     *
GGA GCT GCT GCT GGT GCA GGA GCC GGA GCA GGT AGT ACA GGA GGC TTT
 G   A   A   A   G   A   G   A   G   A   G   S   T   G   G   F>

50          60          70          80          90
  *     *     *     *     *     *     *     *     *     *
GGC GGA CAA GGA GGA TAT GGT GCC GGT GCA GGA GCT GCA GCT GCT GGA
 G   G   Q   G   G   Y   G   A   G   A   G   A   A   A   A   G>

100         110         120         130         140
  *     *     *     *     *     *     *     *     *
GCT TTT GCC GGA AGA GCT GGG GGT TAC GGA AGA GCT GCT GGA GCT GCG
 A   F   A   G   R   A   G   G   Y   G   R   A   A   G   A   A>

150         160         170         180         190
  *     *     *     *     *     *     *     *     *     *
GCT GGA ACT GGA GCT GCT GCT GGT GCA GGA GCC GGA GCT GGT AGT ACA
 A   G   T   G   A   A   A   G   A   G   A   G   A   G   S   T>

200         210         220         230         240
  *     *     *     *     *     *     *     *     *     *
GGA GGC TTT GGC GGA CAA AGA GGA TAC GGT GCC GGC AGA AGT AAT GGA
 G   G   F   G   G   Q   R   G   Y   G   A   G   R   S   N   G>
```

FIG. 3B

```
              10           20           30              40
     *      *       *       *      *       *       *       *       *
TAT GGT GGA CAA GGC GGA TAT GGT GCT GGA GCA GGA GCT GGT GCT GCT
 Y   G   G   Q   G   G   Y   G   A   G   A   G   A   G   A   A>

50           60          70           80              90
  *      *       *       *       *       *      *       *       *       *
GCA GCC GCA GGA TAT GGA GCC GGT GCT GGA GGA TAC GGT GGA CAA GCT
 A   A   A   G   Y   G   A   G   A   G   G   Y   G   G   Q   A>

100          110          120          130          140
     *      *       *       *      *       *       *       *       *       *
GGT TAT GGT GCC GGA GCT GGA GCT GGT AGT TCT GCA GGA AAT GCT TTC
 G   Y   G   A   G   A   G   A   G   S   S   A   G   N   A   F>
```

FIG. 3C

```
N-TERMINI:  MiSP1 vs. MiSP2

MiSP1  M N N L L F A V S G Y V S T L G N A I S D A S A Y A N A L S S A I G N V L A N S
MiSP2

MiSP1  G S I S E S T A S S A A A S S V T T T L T
MiSP2                                         . . .

MiSP1  S Y G P A V F Y A P S A S S G G Y G A A A A G A G G Y G A G R G A G
MiSP2  S Y G P S V F Y T P - T S A G S Y G A G A F G A G A S A G V A G T V A

MiSP1  G Y G G G G G Y G G A G A A A A A G A G G Y G A G R G A G A G A
MiSP2  G Y G G Q G G Y G G A G A G S A G G Y G A G A A A A A T A A G A

MiSP1  A A G A G A G G A . . .
MiSP2  G A A A G A G A G . . .

C-TERMINI:  MiSP1 vs. MiSP2

MiSP1  D K E I A C W S R C R Y T V A S T T T S R L S S A A E A S S R H S S A A A S T L V S G
MiSP2  G G Y A S T G V G I G S T V T S T T T S R L S S A E A C S R I S S A A A S T L V S G

MiSP1  G Y L N T A A L P S V H S D D L F A Q Q V G A S S P - V I R Q R S L H Q V L L E I V
MiSP2  G S L N T A A L P S V I S V I H S D L F A Q S S G N E V L R E V L H Q V L L E I V

MiSP1  S S L I H I L S S S S V G W V D F S S V G Q S M Q Q V V M G stop
MiSP2  S S L I H I L S S S S V G V D F S S A A A V G Q S M Q V V M G stop
```

FIG. 4

SEQUENCE LISTING ( 1 ) GENERAL INFORMATION:

( i i i ) NUMBER OF SEQUENCES: 56

( 2 ) INFORMATION FOR SEQ ID NO:1:

( i ) SEQUENCE CHARACTERISTICS:
      ( A ) LENGTH: 2793 base pairs
      ( B ) TYPE: nucleic acid
      ( C ) STRANDEDNESS: double
      ( D ) TOPOLOGY: linear ( i i ) MOLECULE TYPE: cDNA ( i i i ) HYPOTHETICAL: NO ( v i ) ORIGINAL SOURCE:
      ( A ) ORGANISM: Nephila clavipes
      ( F ) TISSUE TYPE: minor ampullate gland ( i x ) FEATURE:
      ( A ) NAME/KEY: CDS
      ( B ) LOCATION: 183..2675
      ( D ) OTHER INFORMATION: /product="N. clavipes minor ampullate silk protein"

( x i ) SEQUENCE DESCRIPTION: SEQ ID NO:1:

| | | | | | |
|---|---|---|---|---|---|
| ACATACTAGG | TTTGGTGCCG | GAGCTGGAGC | TGGTACGTCT | GTGCAGAAAT | ACTTTGCACA | 60 |
| TCACTTCTCC | AATTGCTTCT | CGGGTATTTG | TCAAATGATT | AGTTCTACAA | CTTCTACTGA | 120 |
| TCATGCAGTA | AGTGTTGCTA | CGAGCGTTGC | GCTGAAGTCA | GCTTGGACTT | GATGCAAATG | 180 |
| CTATGAACAA | CTTACTAGGT | GCCGTTAGTG | GATATGTTTC | GACACTAGGC | AACGCTATTT | 240 |
| CTGATGCTTC | GGCATACGCA | AATGCTCTTT | CTTCCGCTAT | AGGAAATGTG | TTAGCTAATT | 300 |
| CCGGTTCAAT | TAGCGAAAGC | ACTGCATCTT | CTGCTGCTTC | CAGTGCTGCT | TCTTCAGTCA | 360 |
| CTACAACTTT | GACGTCTTAT | GGACCAGCTG | TATTTTACGC | ACCTTCTGCA | TCATCTGGAG | 420 |
| GCTATGGAGC | TGGAGCTGGA | GCTGTTGCTG | CAGCAGGAGC | TGCCGGCGCT | GGAGGTTACG | 480 |
| GAAGAGGTGC | TGGAGGCTAC | GGTGGACAAG | GAGGATATGG | TGCCGGAGCC | GGAGCTGGTG | 540 |
| CTGCTGCAGC | TGCTGGAGCA | GGAGCCGGAG | GCGCTGGTGG | TTACGGTAGA | GGTGCTGGTG | 600 |
| CTGGAGCTGG | TGCGGCTGCT | GGGGCAGGTG | CAGGCGCCGG | TGGTGCTGGA | TATGGTGGAC | 660 |
| AAGGCGGATA | TGGTGCCGGA | GCAGGAGCTG | GTGCGGCTGC | TGCTGCTGGT | GCAGGAGCAG | 720 |
| GAGGTGCTGG | CGGTTACGGT | AGAGGTGCTG | GTGCTGGAGC | AGGAGCCGCT | GCGGGTGCTG | 780 |
| GAGCTGGAGG | CTACGGTGGT | CAAGGTGGGT | ACGGTGCCGG | AGCAGGAGCT | GGTGCGGCTG | 840 |
| CTGCTGCTGC | TGGAGCAGGA | TCTGGAGGCG | CTGGCGGTTA | CGGTAGAGGT | GCTGGTGCTG | 900 |
| GAGCTGGAGC | CGCTGCAGGT | GCAGGAGCAG | GAGCTGGAAG | CTACGGTGGT | CAAGGATACG | 960 |
| GTGCCGGAGC | AGGAGCTGGT | GCTGCTGCAG | CTGCANNNNN | NNNNNNNNNN | NNNNNNNNNN | 1020 |
| NNNNNNNNNN | NNNNNNNGGT | GCAGGTGCAG | GTGCTGGATA | TGGTGGACAA | GGCGGATATG | 1080 |
| GTGCCGGAGC | AGGAGCTGGT | GCGGCTGCTG | CTGCTGGTGC | AGGAGCTGGA | GGTGCTGGTG | 1140 |
| GTTACGGTAG | AGGTGCTGGT | GCTGGAGCTG | GAGCCGCTGC | AGGTGCAGGA | GCAGGAGCTG | 1200 |
| GAGGCTACGG | TGGTCAAAGT | GGATACGGTG | CCGGAGCAGG | AGCTGCTGCA | GCTGCTGGAG | 1260 |
| CAGGAGCTGG | AGGCGCTGGT | GGTTACGGTG | AGGTGCTGGT | GCTGGAGCAG | GAGCCGCTGC | 1320 |

-continued

```
GGGTGCTGGA GCAGGAGCCG CTGCGGGTGC AGGAGCTGGA GGCTACGGTG GTCAAGGTGG      1380
GTACGGTGCC GGTGCAGGAG CTGGTGCGGC TGCTGCTGCT GGAGCAGGAG CTGGAGGCGC      1440
TGGTGGTTAC GGTAGAGGTG CTGGTGCTGG AGCTGGAGCT GCTGCAGGCG CAGGAGCTGG      1500
AGGCTACGGT GGTCAAGGTG GATACGGTGC CGGAGCAGGA GCTGGTGCTG CTGCAGCTGC      1560
TGCAACAGGA GCCGGAGGCG CTGGTGGTTA CGGTAGAGGT GCTGGTGCTG GAGCTGGTGC      1620
CGCTGCTGGG GCAGGTGCAG GCACCGGTGG TGCTGGATAT GGTGGACAAG GCGGTTATGG      1680
TGCCGGAGCA GGAGCTGGTG CGGCTGCTGC TGCTGGTGCA GGAGCAGGAG GTGCTGGTTA      1740
CGGTAGAGGT GCTGGTGCTG GAGCTGGAGC TGCTGCAGGT GCTGGAGCTG GAGCCGCTGC      1800
AGGTGCAGGA GCAGGAGCTG GAGGCTACGG TGGTCAGGGT GGATACGGTG CCGGAGCAAG      1860
AGCTGGTGCT GCGGCAGCTG CTGGAGCAGG AGCTGGAGGC GCTGCGGGTT ACAGTAGAGG      1920
TGGTCGTGCA GGAGCCGCTG GTGCTGGAGC TGGAGCCGCT GCAGGTGCAG GAGCAGGAGC      1980
TGGAGGCTAC GGTGGTCAAG GTGGATACGG TGCCGGAGCA GGAGCTGGTG CTGCTGCAGC      2040
TGCTGGTGCA GGATCCGGAG GCGCTGGTGG TTACGGTAGA GGTGCTGGTG CTGGAGCCGC      2100
TGCAGGAGCT GGAGCCGCTG CAGGTGCTGG AGCAGGAGCT GGAGGCTACG GTGGTCAAGG      2160
TGGATACGGT GCCGGAGCAG GAGCTGCTGC AGCTGCTGGA GCAGGAGCCG GACGTGGAGG      2220
TTACGGAAGA GGTGCTGGTG CTGGAGGCTA CGGTGGACAA GGAGGATATG GTGCCGGAGC      2280
TGGAGCCGGT GCTGCTGCAG CTGCTGGAGC GGGAGCCGGA GGCTATGGCG ACAAGGAGAT      2340
AGCCTGCTGG AGCAGGTGTA GATACACTGT TGCCTCCACA ACATCTCGTT TGAGTTCGGC      2400
CGAAGCATCT TCTAGGATAT CGTCGGCGGC TTCCACTTTA GTATCTGGAG GTTACTTGAA      2460
TACAGCAGCT CTGCCATCGG TTATTTCGGA TCTTTTTGCC CAAGTTGGTG CATCTTCTCC      2520
GGTGATCAGA CAGCGAAGTT TGATCCAAGT TTTGTTGGAA ATTGTTTCTT CTCTTATCCA      2580
TATTCTCAGT TCTTCTAGCG TAGGACAAGT CGATTTCAGT TCGGTTGGGT CGTCTGCTGC      2640
AGCTGTTGGT CAATCCATGC AAGTTGTAAT GGGCTAAACA TGATGGTTCT CTCAATTATG      2700
TATTCTTTAA TTACCGCTAA GGTAGCAAAA TATTGTAAAG TAAAGTTTTC TTACAAAATA      2760
AAAATTCTTT TCTGCAAAAA AAAAAAAAA  AAA                                   2793
```

( 2 ) INFORMATION FOR SEQ ID NO:2:

( i ) SEQUENCE CHARACTERISTICS:
        ( A ) LENGTH: 832 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( v ) FRAGMENT TYPE: internal ( v i ) ORIGINAL SOURCE:
        ( A ) ORGANISM: N. clavipes
        ( F ) TISSUE TYPE: minor ampullate gland ( i x ) FEATURE:
        ( A ) NAME/KEY: CDS
        ( B ) LOCATION: 1..309

( x i ) SEQUENCE DESCRIPTION: SEQ ID NO:2:

```
Met Asn Asn Leu Leu Gly Ala Val Ser Gly Tyr Val Ser Thr Leu Gly
  1               5                  10                  15

Asn Ala Ile Ser Asp Ala Ser Ala Tyr Ala Asn Ala Leu Ser Ser Ala
```

-continued

```
                              20                      25                        30
     Ile  Gly  Asn  Val  Leu  Ala  Asn  Ser  Gly  Ser  Ile  Ser  Glu  Ser  Thr  Ala
                    35                     40                     45
     Ser  Ser  Ala  Ala  Ser  Ser  Ala  Ala  Ser  Ser  Val  Thr  Thr  Thr  Leu  Thr
               50                     55                     60
     Ser  Tyr  Gly  Pro  Ala  Val  Phe  Tyr  Ala  Pro  Ser  Ala  Ser  Ser  Gly  Gly
     65                          70                     75                          80
     Tyr  Gly  Ala  Gly  Ala  Gly  Ala  Val  Ala  Ala  Ala  Gly  Ala  Ala  Gly  Ala
                         85                     90                          95
     Gly  Gly  Tyr  Gly  Arg  Gly  Ala  Gly  Gly  Tyr  Gly  Gly  Gln  Gly  Gly  Tyr
                         100                    105                    110
     Gly  Ala  Gly  Ala  Gly  Ala  Gly  Ala  Ala  Ala  Ala  Gly  Ala  Gly  Ala
                    115                    120                     125
     Gly  Gly  Ala  Gly  Gly  Tyr  Gly  Arg  Gly  Ala  Gly  Ala  Gly  Ala  Gly  Ala
               130                    135                         140
     Ala  Ala  Gly  Ala  Gly  Ala  Gly  Ala  Gly  Gly  Ala  Gly  Tyr  Gly  Gly  Gln
     145                         150                    155                         160
     Gly  Gly  Tyr  Gly  Ala  Gly  Ala  Gly  Ala  Gly  Ala  Ala  Ala  Ala  Ala  Gly
                         165                    170                         175
     Ala  Gly  Ala  Gly  Gly  Ala  Gly  Gly  Tyr  Gly  Arg  Gly  Ala  Gly  Ala  Gly
                    180                    185                         190
     Ala  Gly  Ala  Ala  Ala  Gly  Ala  Gly  Ala  Gly  Gly  Tyr  Gly  Gly  Gln  Gly
                    195                    200                         205
     Gly  Tyr  Gly  Ala  Gly  Ala  Gly  Ala  Gly  Ala  Ala  Ala  Ala  Ala  Ala  Gly
          210                    215                         220
     Ala  Gly  Ser  Gly  Gly  Ala  Gly  Gly  Tyr  Gly  Arg  Gly  Ala  Gly  Ala  Gly
     225                         230                    235                         240
     Ala  Gly  Ala  Ala  Ala  Gly  Ala  Gly  Ala  Gly  Ala  Gly  Ser  Tyr  Gly  Gly
                         245                    250                         255
     Gln  Gly  Tyr  Gly  Ala  Gly  Ala  Gly  Ala  Gly  Ala  Ala  Ala  Ala  Ala  Xaa
                         260                    265                         270
     Xaa  Xaa  Xaa  Xaa  Xaa  Xaa  Xaa  Xaa  Xaa  Xaa  Xaa  Xaa  Xaa  Xaa  Gly  Ala
                    275                    280                         285
     Gly  Ala  Gly  Ala  Gly  Tyr  Gly  Gly  Gln  Gly  Gly  Tyr  Gly  Ala  Gly  Ala
          290                         295                    300
     Gly  Ala  Gly  Ala  Ala  Ala  Ala  Ala  Gly  Ala  Gly  Ala  Gly  Gly  Ala  Gly
     305                         310                    315                         320
     Gly  Tyr  Gly  Arg  Gly  Ala  Gly  Ala  Gly  Ala  Gly  Ala  Ala  Ala  Gly  Ala
                         325                    330                         335
     Gly  Ala  Gly  Ala  Gly  Gly  Tyr  Gly  Gly  Gln  Ser  Gly  Tyr  Gly  Ala  Gly
                    340                         345                    350
     Ala  Gly  Ala  Ala  Ala  Ala  Ala  Gly  Ala  Gly  Ala  Gly  Gly  Ala  Gly  Gly
               355                    360                    365
     Tyr  Gly  Arg  Gly  Ala  Gly  Ala  Gly  Ala  Gly  Ala  Ala  Ala  Gly  Ala  Gly
          370                         375                    380
     Ala  Gly  Ala  Ala  Ala  Gly  Ala  Gly  Ala  Gly  Gly  Tyr  Gly  Gly  Gln  Gly
     385                         390                    395                         400
     Gly  Tyr  Gly  Ala  Gly  Ala  Gly  Ala  Gly  Ala  Ala  Ala  Ala  Ala  Gly  Ala
                         405                    410                         415
     Gly  Ala  Gly  Gly  Ala  Gly  Gly  Tyr  Gly  Arg  Gly  Ala  Gly  Ala  Gly  Ala
                    420                    425                         430
     Gly  Ala  Ala  Ala  Gly  Ala  Gly  Ala  Gly  Gly  Tyr  Gly  Gly  Gln  Gly  Gly
                    435                    440                         445
```

```
Tyr Gly Ala Gly Ala Gly Ala Gly Ala Ala Ala Ala Ala Ala Thr Gly
    450             455             460
Ala Gly Gly Ala Gly Gly Tyr Gly Arg Gly Ala Gly Ala Gly Ala Gly
465             470             475             480
Ala Ala Ala Gly Ala Gly Ala Gly Thr Gly Gly Ala Gly Tyr Gly Gly
            485             490             495
Gln Gly Gly Tyr Gly Ala Gly Ala Gly Ala Gly Ala Ala Ala Ala Ala
            500             505             510
Gly Ala Gly Ala Gly Gly Ala Gly Tyr Gly Arg Gly Ala Gly Ala Gly
        515             520             525
Ala Gly Ala Ala Ala Gly Ala Gly Ala Gly Ala Ala Ala Gly Ala Gly
        530             535             540
Ala Gly Ala Gly Gly Tyr Gly Gly Gln Gly Gly Tyr Gly Ala Gly Ala
545             550             555             560
Arg Ala Gly Ala Ala Ala Ala Ala Gly Ala Gly Ala Gly Gly Ala Ala
            565             570             575
Gly Tyr Ser Arg Gly Gly Arg Ala Gly Ala Ala Gly Ala Gly Ala Gly
            580             585             590
Ala Ala Ala Gly Ala Gly Ala Gly Ala Gly Gly Tyr Gly Gly Gln Gly
            595             600             605
Gly Tyr Gly Ala Gly Ala Gly Ala Gly Ala Ala Ala Ala Ala Gly Ala
    610             615             620
Gly Ser Gly Gly Ala Gly Gly Tyr Gly Arg Gly Ala Gly Ala Gly Ala
625             630             635             640
Ala Ala Gly Ala Gly Ala Ala Ala Gly Ala Gly Ala Gly Ala Gly Gly
            645             650             655
Tyr Gly Gly Gln Gly Gly Tyr Gly Ala Gly Ala Gly Ala Ala Ala Ala
            660             665             670
Ala Gly Ala Gly Ala Gly Arg Gly Gly Tyr Gly Arg Gly Ala Gly Ala
        675             680             685
Gly Gly Tyr Gly Gly Gln Gly Gly Tyr Gly Ala Gly Ala Gly Ala Gly
    690             695             700
Ala Ala Ala Ala Ala Gly Ala Gly Ala Gly Gly Tyr Gly Asp Lys Glu
705             710             715             720
Ile Ala Cys Trp Ser Arg Cys Arg Tyr Thr Val Ala Ser Thr Thr Ser
            725             730             735
Arg Leu Ser Ser Ala Glu Ala Ser Ser Arg Ile Ser Ser Ala Ala Ser
            740             745             750
Thr Leu Val Ser Gly Gly Tyr Leu Asn Thr Ala Ala Leu Pro Ser Val
        755             760             765
Ile Ser Asp Leu Phe Ala Gln Val Gly Ala Ser Ser Pro Val Ile Arg
    770             775             780
Gln Arg Ser Leu Ile Gln Val Leu Leu Glu Ile Val Ser Ser Leu Ile
785             790             795             800
His Ile Leu Ser Ser Ser Ser Val Gly Gln Val Asp Phe Ser Ser Val
            805             810             815
Gly Ser Ser Ala Ala Ala Val Gly Gln Ser Met Gln Val Val Met Gly
            820             825             830
```

( 2 ) INFORMATION FOR SEQ ID NO:3:

( i ) SEQUENCE CHARACTERISTICS:
        ( A ) LENGTH: 309 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( v i ) ORIGINAL SOURCE:
  ( A ) ORGANISM: N. clavipes
  ( F ) TISSUE TYPE: minor ampullate gland ( i x ) FEATURE:
  ( A ) NAME/KEY: CDS
  ( B ) LOCATION: 1..309
  ( D ) OTHER INFORMATION: /product="amino terminus of MISP2 protein"

( x i ) SEQUENCE DESCRIPTION: SEQ ID NO:3:

| | | | | | | | | | | | | | | | | |
|---|---|---|---|---|---|---|---|---|---|---|---|---|---|---|---|---|
| TCT | TAT | GGA | CCA | TCC | GTA | TTT | TAC | ACT | CCT | ACT | TCA | GCT | GGA | AGC | TAT | 48 |
| Ser | Tyr | Gly | Pro | Ser | Val | Phe | Tyr | Thr | Pro | Thr | Ser | Ala | Gly | Ser | Tyr | |
| 1 | | | | 5 | | | | | 10 | | | | | 15 | | |
| GGT | GCA | GGG | GCC | GGA | GGT | TTT | GGA | GCT | GGA | GCC | TCT | GCT | GGT | GTC | GGA | 96 |
| Gly | Ala | Gly | Ala | Gly | Gly | Phe | Gly | Ala | Gly | Ala | Ser | Ala | Gly | Val | Gly | |
| | | | 20 | | | | | 25 | | | | | 30 | | | |
| GCC | GGA | GCT | GGT | ACT | GTA | GCA | GGA | TAT | GGT | GGA | CAA | GGA | GGA | TAT | GGT | 144 |
| Ala | Gly | Ala | Gly | Thr | Val | Ala | Gly | Tyr | Gly | Gly | Gln | Gly | Gly | Tyr | Gly | |
| | | | 35 | | | | | 40 | | | | | 45 | | | |
| GCC | GGA | AGC | GCT | GGA | GGT | TAT | GGA | AGA | GGT | ACT | GGA | GCT | GGA | GCC | GCT | 192 |
| Ala | Gly | Ser | Ala | Gly | Gly | Tyr | Gly | Arg | Gly | Thr | Gly | Ala | Gly | Ala | Ala | |
| | | 50 | | | | | 55 | | | | | 60 | | | | |
| GCT | GGT | GCC | GGA | GCA | GGA | GCC | ACT | GCT | GGT | GCC | GGA | GCA | GGA | GCC | GCT | 240 |
| Ala | Gly | Ala | Gly | Ala | Gly | Ala | Thr | Ala | Gly | Ala | Gly | Ala | Gly | Ala | Ala | |
| 65 | | | | | 70 | | | | | 75 | | | | | 80 | |
| GCT | GGT | GCC | GGA | GCA | GGA | GCA | GGT | AAT | TCA | GGA | GGA | TAT | AGT | GCC | GGA | 288 |
| Ala | Gly | Ala | Gly | Ala | Gly | Ala | Gly | Asn | Ser | Gly | Gly | Tyr | Ser | Ala | Gly | |
| | | | | 85 | | | | | 90 | | | | | 95 | | |
| GTA | GGA | GTT | GGT | GCT | GCA | GCT | | | | | | | | | | 309 |
| Val | Gly | Val | Gly | Ala | Ala | Ala | | | | | | | | | | |
| | | | 100 | | | | | | | | | | | | | |

( 2 ) INFORMATION FOR SEQ ID NO:4:

( i ) SEQUENCE CHARACTERISTICS:
  ( A ) LENGTH: 103 amino acids
  ( B ) TYPE: amino acid
  ( D ) TOPOLOGY: linear ( i i ) MOLECULE TYPE: protein ( x i ) SEQUENCE DESCRIPTION: SEQ ID NO:4:

| | | | | | | | | | | | | | | | |
|---|---|---|---|---|---|---|---|---|---|---|---|---|---|---|---|
| Ser | Tyr | Gly | Pro | Ser | Val | Phe | Tyr | Thr | Pro | Thr | Ser | Ala | Gly | Ser | Tyr |
| 1 | | | | 5 | | | | | 10 | | | | | 15 | |
| Gly | Ala | Gly | Ala | Gly | Gly | Phe | Gly | Ala | Gly | Ala | Ser | Ala | Gly | Val | Gly |
| | | | 20 | | | | | 25 | | | | | 30 | | |
| Ala | Gly | Ala | Gly | Thr | Val | Ala | Gly | Tyr | Gly | Gly | Gln | Gly | Gly | Tyr | Gly |
| | | | 35 | | | | | 40 | | | | | 45 | | |
| Ala | Gly | Ser | Ala | Gly | Gly | Tyr | Gly | Arg | Gly | Thr | Gly | Ala | Gly | Ala | Ala |
| | | 50 | | | | | 55 | | | | | 60 | | | |
| Ala | Gly | Ala | Gly | Ala | Gly | Ala | Thr | Ala | Gly | Ala | Gly | Ala | Gly | Ala | Ala |
| 65 | | | | | 70 | | | | | 75 | | | | | 80 |
| Ala | Gly | Ala | Gly | Ala | Gly | Ala | Gly | Asn | Ser | Gly | Gly | Tyr | Ser | Ala | Gly |
| | | | | 85 | | | | | 90 | | | | | 95 | |
| Val | Gly | Val | Gly | Ala | Ala | Ala | | | | | | | | | |
| | | | 100 | | | | | | | | | | | | |

( 2 ) INFORMATION FOR SEQ ID NO:5:

( i ) SEQUENCE CHARACTERISTICS:
   ( A ) LENGTH: 165 base pairs
   ( B ) TYPE: nucleic acid
   ( C ) STRANDEDNESS: double
   ( D ) TOPOLOGY: linear ( i i ) MOLECULE TYPE: cDNA ( i i i ) HYPOTHETICAL: NO ( v i ) ORIGINAL SOURCE:
   ( A ) ORGANISM: N. clavipes
   ( F ) TISSUE TYPE: minor ampullate gland ( i x ) FEATURE:
   ( A ) NAME/KEY: CDS
   ( B ) LOCATION: 3..164
   ( D ) OTHER INFORMATION: /product="an internal portion of MISP2"

( x i ) SEQUENCE DESCRIPTION: SEQ ID NO:5:

```
CT GCA GCT GCT GGA GGA GGT GCC GGA ACT GTT GGA GGT TAC GGA AGA      47
   Ala Ala Ala Gly Gly Gly Ala Gly Thr Val Gly Gly Tyr Gly Arg
   1               5                   10                  15

GGT GCT GGT GTA GGA GCA GGT GCC GCT GCT GGT TTT GCG GCA GGA GCT     95
Gly Ala Gly Val Gly Ala Gly Ala Ala Ala Gly Phe Ala Ala Gly Ala
                20                  25                  30

GGT GGT GCT GGA GGC TAC AGA AGA GAT GGA GGA TAC GGT GCT GGA GCA    143
Gly Gly Ala Gly Gly Tyr Arg Arg Asp Gly Gly Tyr Gly Ala Gly Ala
            35                  40                  45

GGA GCT GGA GCT GCT GCA GCT G                                      165
Gly Ala Gly Ala Ala Ala Ala
        50
```

( 2 ) INFORMATION FOR SEQ ID NO:6:

( i ) SEQUENCE CHARACTERISTICS:
      ( A ) LENGTH: 54 amino acids
      ( B ) TYPE: amino acid
      ( D ) TOPOLOGY: linear ( i i ) MOLECULE TYPE: protein ( x i ) SEQUENCE DESCRIPTION: SEQ ID NO:6:

```
Ala Ala Ala Gly Gly Gly Ala Gly Thr Val Gly Gly Tyr Gly Arg Gly
1               5                   10                  15

Ala Gly Val Gly Ala Gly Ala Ala Ala Gly Phe Ala Ala Gly Ala Gly
            20                  25                  30

Gly Ala Gly Gly Tyr Arg Arg Asp Gly Gly Tyr Gly Ala Gly Ala Gly
        35                  40                  45

Ala Gly Ala Ala Ala Ala
    50
```

( 2 ) INFORMATION FOR SEQ ID NO:7:

( i ) SEQUENCE CHARACTERISTICS:
      ( A ) LENGTH: 870 base pairs
      ( B ) TYPE: nucleic acid
      ( C ) STRANDEDNESS: double
      ( D ) TOPOLOGY: linear ( i i ) MOLECULE TYPE: cDNA ( i i i ) HYPOTHETICAL: NO ( v i ) ORIGINAL SOURCE:
      ( A ) ORGANISM: N. clavipes
      ( F ) TISSUE TYPE: minor ampullate gland ( i x ) FEATURE:
    ( A ) NAME/KEY: CDS
    ( B ) LOCATION: 1..753
    ( D ) OTHER INFORMATION: /product="MISP2 carboxy terminus"

( x i ) SEQUENCE DESCRIPTION: SEQ ID NO:7:

```
GGT  GCA  GGA  GGC  TAT  GGA  AGA  GGT  GCT  GGA  GCT  GGA  GCT  GCT  GCA  GTC        48
Gly  Ala  Gly  Gly  Tyr  Gly  Arg  Gly  Ala  Gly  Ala  Gly  Ala  Ala  Ala  Val
 1                    5                        10                       15

GCA  GGT  GCA  GAT  GCT  GGT  GGC  TAT  GGA  AGA  AAT  TAT  GGT  GCT  GGA  ACC        96
Ala  Gly  Ala  Asp  Ala  Gly  Gly  Tyr  Gly  Arg  Asn  Tyr  Gly  Ala  Gly  Thr
               20                        25                       30

ACT  GCT  TAT  GCA  GGA  GCC  AGA  GCC  GGT  GGT  GCT  GGA  GGC  TAT  GGC  GGA       144
Thr  Ala  Tyr  Ala  Gly  Ala  Arg  Ala  Gly  Gly  Ala  Gly  Gly  Tyr  Gly  Gly
          35                        40                       45

CAA  GGA  GGA  TAT  TCT  TCT  GGA  GCC  GGT  GCT  GCT  GCA  GCT  TCT  GGA  GCA       192
Gln  Gly  Gly  Tyr  Ser  Ser  Gly  Ala  Gly  Ala  Ala  Ala  Ala  Ser  Gly  Ala
     50                        55                       60

GGA  GCC  GAT  ATC  ACT  AGT  GGA  TAC  GGA  AGA  GGT  GTT  GGT  GCT  GGA  GCT       240
Gly  Ala  Asp  Ile  Thr  Ser  Gly  Tyr  Gly  Arg  Gly  Val  Gly  Ala  Gly  Ala
65                       70                        75                       80

GGA  GCA  GAA  ACT  ATA  GGT  GCT  GGA  GGC  TAT  GGA  GGT  GGG  GCT  GGA  TCA       288
Gly  Ala  Glu  Thr  Ile  Gly  Ala  Gly  Gly  Tyr  Gly  Gly  Gly  Ala  Gly  Ser
                    85                        90                       95

GGA  GCA  CGT  GCG  GCT  TCA  GCA  TCC  GGA  GCT  GGT  ACT  GGA  TAT  GGT  TCG       336
Gly  Ala  Arg  Ala  Ala  Ser  Ala  Ser  Gly  Ala  Gly  Thr  Gly  Tyr  Gly  Ser
               100                      105                     110

TCT  GGA  GGT  TAT  AAC  GTA  GGT  ACC  GGA  ATA  AGT  ACT  TCT  TCT  GGC  GCT       384
Ser  Gly  Gly  Tyr  Asn  Val  Gly  Thr  Gly  Ile  Ser  Thr  Ser  Ser  Gly  Ala
          115                      120                     125

GCA  TCT  AGC  TAC  TCT  GTT  TCT  GCT  GGA  GGT  TAT  GCT  TCA  ACA  GGT  GTT       432
Ala  Ser  Ser  Tyr  Ser  Val  Ser  Ala  Gly  Gly  Tyr  Ala  Ser  Thr  Gly  Val
     130                      135                      140

GGT  ATT  GGA  TCC  ACT  GTT  ACA  TCC  ACA  ACA  TCT  CGT  TTG  AGT  TCT  GCT       480
Gly  Ile  Gly  Ser  Thr  Val  Thr  Ser  Thr  Thr  Ser  Arg  Leu  Ser  Ser  Ala
145                      150                      155                     160

GAA  GCA  TGT  TCT  AGA  ATA  TCT  GCT  GCG  GCT  TCC  ACT  TTA  GTA  TCT  GGA       528
Glu  Ala  Cys  Ser  Arg  Ile  Ser  Ala  Ala  Ala  Ser  Thr  Leu  Val  Ser  Gly
                    165                      170                     175

TCC  TTG  AAT  ACT  GCA  GCT  TTA  CCA  TCT  GTA  ATT  TCG  GAT  CTT  TTT  GCC       576
Ser  Leu  Asn  Thr  Ala  Ala  Leu  Pro  Ser  Val  Ile  Ser  Asp  Leu  Phe  Ala
               180                      185                     190

CAA  GTT  AGT  GCA  TCA  TCA  CCC  GGG  GTA  TCA  GGT  AAC  GAA  GTT  TTG  ATT       624
Gln  Val  Ser  Ala  Ser  Ser  Pro  Gly  Val  Ser  Gly  Asn  Glu  Val  Leu  Ile
     195                      200                      205

CAA  GTT  TTG  TTG  GAA  ATT  GTT  TCT  TCT  CTT  ATC  CAT  ATT  CTT  AGT  TCT       672
Gln  Val  Leu  Leu  Glu  Ile  Val  Ser  Ser  Leu  Ile  His  Ile  Leu  Ser  Ser
     210                      215                      220

TCT  AGT  GTA  GGG  CAA  GTA  GAT  TTC  AGT  TCT  GTT  GGT  TCA  TCT  GCT  GCA       720
Ser  Ser  Val  Gly  Gln  Val  Asp  Phe  Ser  Ser  Val  Gly  Ser  Ser  Ala  Ala
225                      230                      235                     240

GCC  GTT  GGT  CAA  TCC  ATG  CAA  GTT  GTA  ATG  GGT  TAAACAAAA  TGGCTCTCTC         773
Ala  Val  Gly  Gln  Ser  Met  Gln  Val  Val  Met  Gly
                    245                      250

TCTGTTATAT  GCATTCTGTA  ATTTCTTCTA  AACTATTAAA  ATAATGTAAT  AATTTCCTGC            833

ATAAATAAAA  ATATTTTTCT  GCAAAAAAAA  AAAAAAA                                       870
```

( 2 ) INFORMATION FOR SEQ ID NO:8:

( i ) SEQUENCE CHARACTERISTICS:
        ( A ) LENGTH: 251 amino acids (B) TYPE: amino acid
(D) TOPOLOGY: linear (ii) MOLECULE TYPE: protein (xi) SEQUENCE DESCRIPTION: SEQ ID NO:8:

```
Gly Ala Gly Gly Tyr Gly Arg Gly Ala Gly Ala Gly Ala Ala Val
 1               5                  10                  15

Ala Gly Ala Asp Ala Gly Gly Tyr Gly Arg Asn Tyr Gly Ala Gly Thr
             20                  25                  30

Thr Ala Tyr Ala Gly Ala Arg Ala Gly Gly Ala Gly Gly Tyr Gly Gly
             35                  40                      45

Gln Gly Gly Tyr Ser Ser Gly Ala Gly Ala Ala Ala Ser Gly Ala
         50                  55                  60

Gly Ala Asp Ile Thr Ser Gly Tyr Gly Arg Gly Val Gly Ala Gly Ala
 65                  70                  75                  80

Gly Ala Glu Thr Ile Gly Ala Gly Gly Tyr Gly Gly Gly Ala Gly Ser
                 85                  90                      95

Gly Ala Arg Ala Ala Ser Ala Ser Gly Ala Gly Thr Gly Tyr Gly Ser
             100                 105                 110

Ser Gly Gly Tyr Asn Val Gly Thr Gly Ile Ser Thr Ser Ser Gly Ala
         115                 120                 125

Ala Ser Ser Tyr Ser Val Ser Ala Gly Gly Tyr Ala Ser Thr Gly Val
     130                 135                 140

Gly Ile Gly Ser Thr Val Thr Ser Thr Thr Ser Arg Leu Ser Ser Ala
145                 150                 155                 160

Glu Ala Cys Ser Arg Ile Ser Ala Ala Ala Ser Thr Leu Val Ser Gly
             165                 170                 175

Ser Leu Asn Thr Ala Ala Leu Pro Ser Val Ile Ser Asp Leu Phe Ala
             180                 185                 190

Gln Val Ser Ala Ser Ser Pro Gly Val Ser Gly Asn Glu Val Leu Ile
         195                 200                 205

Gln Val Leu Leu Glu Ile Val Ser Ser Leu Ile His Ile Leu Ser Ser
     210                 215                 220

Ser Ser Val Gly Gln Val Asp Phe Ser Ser Val Gly Ser Ser Ala Ala
225                 230                 235                 240

Ala Val Gly Gln Ser Met Gln Val Val Met Gly
             245                 250
```

(2) INFORMATION FOR SEQ ID NO:9:

(i) SEQUENCE CHARACTERISTICS:
    (A) LENGTH: 165 base pairs
    (B) TYPE: nucleic acid
    (C) STRANDEDNESS: double
    (D) TOPOLOGY: linear (ii) MOLECULE TYPE: cDNA (iii) HYPOTHETICAL: NO (vi) ORIGINAL SOURCE:
    (A) ORGANISM: N. clavipes
    (F) TISSUE TYPE: minor ampullate gland (ix) FEATURE:
    (A) NAME/KEY: -
    (B) LOCATION: 1..165
    (D) OTHER INFORMATION: /label=cloned_cDNA
        / note= "pMISS3 partial sequence, 11-1 template,
        forward primer"

(ix) FEATURE:

( A ) NAME/KEY: CDS
( B ) LOCATION: 1..165
( D ) OTHER INFORMATION: /product="translation of pMISS3 partial sequence"

( x i ) SEQUENCE DESCRIPTION: SEQ ID NO:9:

| GCT | GGA | GCT | GCT | GCT | GGT | GCT | GGA | GGC | TAT | GAC | GGA | CAA | GGA | GGA | TAT | 48 |
|---|---|---|---|---|---|---|---|---|---|---|---|---|---|---|---|---|
| Ala | Gly | Ala | Ala | Ala | Gly | Ala | Gly | Gly | Tyr | Asp | Gly | Gln | Gly | Gly | Tyr | |
| 1 | | | | 5 | | | | | 10 | | | | | 15 | | |

| GGT | GCT | GGA | GCA | GGA | GCT | GCT | GCA | GCT | GCT | GGA | GCA | GGA | GCC | GGA | AGC | 96 |
|---|---|---|---|---|---|---|---|---|---|---|---|---|---|---|---|---|
| Gly | Ala | Gly | Ala | Gly | Ala | Ala | Ala | Ala | Ala | Gly | Ala | Gly | Ala | Gly | Ser | |
| | | | 20 | | | | | 25 | | | | | 30 | | | |

| GTT | GGA | GGT | TAT | GGA | ACA | GGT | GCT | GTA | GCT | GGA | TCT | GGA | ACA | GCT | GCT | 144 |
|---|---|---|---|---|---|---|---|---|---|---|---|---|---|---|---|---|
| Val | Gly | Gly | Tyr | Gly | Thr | Gly | Ala | Val | Ala | Gly | Ser | Gly | Thr | Ala | Ala | |
| | | 35 | | | | | 40 | | | | | 45 | | | | |

| GGT | GCA | GGA | GCC | AGA | GCT | GGT | | | | | | | | | | 165 |
|---|---|---|---|---|---|---|---|---|---|---|---|---|---|---|---|---|
| Gly | Ala | Gly | Ala | Arg | Ala | Gly | | | | | | | | | | |
| 50 | | | | | 55 | | | | | | | | | | | |

( 2 ) INFORMATION FOR SEQ ID NO:10:

( i ) SEQUENCE CHARACTERISTICS:
( A ) LENGTH: 55 amino acids
( B ) TYPE: amino acid
( D ) TOPOLOGY: linear ( i i ) MOLECULE TYPE: protein ( x i ) SEQUENCE DESCRIPTION: SEQ ID NO:10:

| Ala | Gly | Ala | Ala | Ala | Gly | Ala | Gly | Gly | Tyr | Asp | Gly | Gln | Gly | Gly | Tyr |
|---|---|---|---|---|---|---|---|---|---|---|---|---|---|---|---|
| 1 | | | | 5 | | | | | 10 | | | | | 15 | |

| Gly | Ala | Gly | Ala | Gly | Ala | Ala | Ala | Ala | Ala | Gly | Ala | Gly | Ala | Gly | Ser |
|---|---|---|---|---|---|---|---|---|---|---|---|---|---|---|---|
| | | | 20 | | | | | 25 | | | | | 30 | | |

| Val | Gly | Gly | Tyr | Gly | Thr | Gly | Ala | Val | Ala | Gly | Ser | Gly | Thr | Ala | Ala |
|---|---|---|---|---|---|---|---|---|---|---|---|---|---|---|---|
| | | 35 | | | | | 40 | | | | | 45 | | | |

| Gly | Ala | Gly | Ala | Arg | Ala | Gly |
|---|---|---|---|---|---|---|
| 50 | | | | | 55 | |

( 2 ) INFORMATION FOR SEQ ID NO:11:

( i ) SEQUENCE CHARACTERISTICS:
( A ) LENGTH: 240 base pairs
( B ) TYPE: nucleic acid
( C ) STRANDEDNESS: double
( D ) TOPOLOGY: linear ( i i ) MOLECULE TYPE: cDNA ( v i ) ORIGINAL SOURCE:
( A ) ORGANISM: N. clavipes
( F ) TISSUE TYPE: minor ampullate gland ( i x ) FEATURE:
( A ) NAME/KEY: -
( B ) LOCATION: 1..240
( D ) OTHER INFORMATION: /label=cloned_cDNA
/ note= "partial sequence of pMISS3, 11-1 template, reverse primer"

( i x ) FEATURE:
( A ) NAME/KEY: CDS
( B ) LOCATION: 1..240
( D ) OTHER INFORMATION: /product="pMISS3 partial sequence translation"

( x i ) SEQUENCE DESCRIPTION: SEQ ID NO:11:

| GGA | GCT | GCT | GCT | GGT | GCA | GGA | GCC | GGA | GCA | GGT | AGT | ACA | GGA | GGC | TTT | 48 |
|---|---|---|---|---|---|---|---|---|---|---|---|---|---|---|---|---|
| Gly | Ala | Ala | Ala | Gly | Ala | Gly | Ala | Gly | Ala | Gly | Ser | Thr | Gly | Gly | Phe | |
| 1 | | | | 5 | | | | | 10 | | | | | 15 | | |

```
GGC GGA CAA GGA GGA TAT GGT GCC GGT GCA GGA GCT GCA GCT GCT GGA        96
Gly Gly Gln Gly Gly Tyr Gly Ala Gly Ala Gly Ala Ala Ala Ala Gly
            20                  25                  30

GCT TTT GCC GGA AGA GCT GGG GGT TAC GGA AGA GCT GCT GGA GCT GCG       144
Ala Phe Ala Gly Arg Ala Gly Gly Tyr Gly Arg Ala Ala Gly Ala Ala
        35                  40                  45

GCT GGA ACT GGA GCT GCT GCT GGT GCA GGA GCC GGA GCT GGT AGT ACA       192
Ala Gly Thr Gly Ala Ala Ala Gly Ala Gly Ala Gly Ala Gly Ser Thr
    50                  55                  60

GGA GGC TTT GGC GGA CAA AGA GGA TAC GGT GCC GGC AGA AGT AAT GGA       240
Gly Gly Phe Gly Gly Gln Arg Gly Tyr Gly Ala Gly Arg Ser Asn Gly
65                  70                  75                  80
```

(2) INFORMATION FOR SEQ ID NO:12:

(i) SEQUENCE CHARACTERISTICS:
        (A) LENGTH: 80 amino acids
        (B) TYPE: amino acid
        (D) TOPOLOGY: linear (ii) MOLECULE TYPE: protein (xi) SEQUENCE DESCRIPTION: SEQ ID NO:12:

```
Gly Ala Ala Ala Gly Ala Gly Ala Gly Ala Gly Ser Thr Gly Gly Phe
1               5                   10                  15

Gly Gly Gln Gly Gly Tyr Gly Ala Gly Ala Gly Ala Ala Ala Ala Gly
            20                  25                  30

Ala Phe Ala Gly Arg Ala Gly Gly Tyr Gly Arg Ala Ala Gly Ala Ala
        35                  40                  45

Ala Gly Thr Gly Ala Ala Ala Gly Ala Gly Ala Gly Ala Gly Ser Thr
    50                  55                  60

Gly Gly Phe Gly Gly Gln Arg Gly Tyr Gly Ala Gly Arg Ser Asn Gly
65                  70                  75                  80
```

(2) INFORMATION FOR SEQ ID NO:13:

(i) SEQUENCE CHARACTERISTICS:
        (A) LENGTH: 144 base pairs
        (B) TYPE: nucleic acid
        (C) STRANDEDNESS: double
        (D) TOPOLOGY: linear (ii) MOLECULE TYPE: cDNA (vi) ORIGINAL SOURCE:
        (A) ORGANISM: N. clavipes
        (F) TISSUE TYPE: minor ampullate gland (ix) FEATURE:
        (A) NAME/KEY: -
        (B) LOCATION: 1..144
        (D) OTHER INFORMATION: /label=cloned_cDNA
        / note="partial sequence of pMISS3, 11-2 template,
        forward primer"

(ix) FEATURE:
        (A) NAME/KEY: CDS
        (B) LOCATION: 1..144
        (D) OTHER INFORMATION: /product="translation of pMISS3
        partial sequence"

(xi) SEQUENCE DESCRIPTION: SEQ ID NO:13:

```
TAT GGT GGA CAA GGC GGA TAT GGT GCT GGA GCA GGA GCT GGT GCT GCT        48
Tyr Gly Gly Gln Gly Gly Tyr Gly Ala Gly Ala Gly Ala Gly Ala Ala
1               5                   10                  15

GCA GCC GCA GGA TAT GGA GCC GGT GCT GGA GGA TAC GGT GGA CAA GCT        96
Ala Ala Ala Gly Tyr Gly Ala Gly Ala Gly Gly Tyr Gly Gly Gln Ala
```

|  |  | 20 |  |  |  | 25 |  |  |  | 30 |  |  |  |  |  |
|---|---|---|---|---|---|---|---|---|---|---|---|---|---|---|---|
| GGT | TAT | GGT | GCC | GGA | GCT | GGA | GCT | GGT | AGT | TCT | GCA | GGA | AAT | GCT | TTC | 144 |
| Gly | Tyr | Gly | Ala | Gly | Ala | Gly | Ala | Gly | Ser | Ser | Ala | Gly | Asn | Ala | Phe |
|  |  | 35 |  |  |  | 40 |  |  |  | 45 |  |  |  |  |  |

( 2 ) INFORMATION FOR SEQ ID NO:14:

( i ) SEQUENCE CHARACTERISTICS:
        ( A ) LENGTH: 48 amino acids
        ( B ) TYPE: amino acid
        ( D ) TOPOLOGY: linear ( i i ) MOLECULE TYPE: protein ( x i ) SEQUENCE DESCRIPTION: SEQ ID NO:14:

```
Tyr  Gly  Gly  Gln  Gly  Gly  Tyr  Gly  Ala  Gly  Ala  Gly  Ala  Gly  Ala  Ala
 1                 5                        10                       15

Ala  Ala  Ala  Gly  Tyr  Gly  Ala  Gly  Ala  Gly  Gly  Tyr  Gly  Gly  Gln  Ala
               20                       25                       30

Gly  Tyr  Gly  Ala  Gly  Ala  Gly  Ala  Gly  Ser  Ser  Ala  Gly  Asn  Ala  Phe
               35                       40                       45
```

( 2 ) INFORMATION FOR SEQ ID NO:15:

( i ) SEQUENCE CHARACTERISTICS:
        ( A ) LENGTH: 155 amino acids
        ( B ) TYPE: amino acid
        ( C ) STRANDEDNESS: single
        ( D ) TOPOLOGY: linear ( i i ) MOLECULE TYPE: peptide ( v ) FRAGMENT TYPE: N-terminal ( i x ) FEATURE:
        ( A ) NAME/KEY: Peptide
        ( B ) LOCATION: 1..155
        ( D ) OTHER INFORMATION: /label=MISPN_aa
            / note= "amino-terminal sequence of misp1, see Fig. 4"

( x i ) SEQUENCE DESCRIPTION: SEQ ID NO:15:

```
Met  Asn  Asn  Leu  Leu  Phe  Ala  Val  Ser  Gly  Tyr  Val  Ser  Thr  Leu  Gly
 1                 5                        10                       15

Asn  Ala  Ile  Ser  Asp  Ala  Ser  Ala  Tyr  Ala  Asn  Ala  Leu  Ser  Ser  Ala
               20                       25                       30

Ile  Gly  Asn  Val  Leu  Ala  Asn  Ser  Gly  Ser  Ile  Ser  Glu  Ser  Thr  Ala
               35                       40                       45

Ser  Ser  Ala  Ala  Ser  Ser  Ala  Ala  Ser  Ser  Val  Thr  Thr  Thr  Leu  Thr
 50                      55                       60

Ser  Tyr  Gly  Pro  Ala  Val  Phe  Tyr  Ala  Pro  Ser  Ala  Ser  Ser  Gly  Gly
 65                      70                       75                       80

Tyr  Gly  Ala  Gly  Ala  Gly  Ala  Val  Ala  Ala  Ala  Gly  Ala  Ala  Gly  Ala
                    85                       90                       95

Gly  Gly  Tyr  Gly  Arg  Gly  Ala  Gly  Gly  Tyr  Gly  Gly  Gln  Gly  Gly  Tyr
               100                      105                      110

Gly  Ala  Gly  Ala  Gly  Ala  Gly  Ala  Ala  Ala  Ala  Ala  Gly  Ala  Gly  Ala
               115                      120                      125

Gly  Gly  Ala  Gly  Gly  Tyr  Gly  Arg  Gly  Ala  Gly  Ala  Gly  Ala  Gly  Ala
               130                      135                      140

Ala  Ala  Gly  Ala  Gly  Ala  Gly  Ala  Gly  Gly  Ala
145                      150                      155
```

( 2 ) INFORMATION FOR SEQ ID NO:16:

( i ) SEQUENCE CHARACTERISTICS:
        ( A ) LENGTH: 90 amino acids
        ( B ) TYPE: amino acid
        ( D ) TOPOLOGY: linear ( i i ) MOLECULE TYPE: peptide ( v ) FRAGMENT TYPE: N-terminal ( i x ) FEATURE:
        ( A ) NAME/KEY: Peptide
        ( B ) LOCATION: 1..90
        ( D ) OTHER INFORMATION: /label=MISP2N_AA
            / note= "amino terminal peptide of MISP2, see Fig. 4"

( x i ) SEQUENCE DESCRIPTION: SEQ ID NO:16:

```
Ser Tyr Gly Pro Ser Val Phe Tyr Thr Pro Thr Ser Ala Gly Ser Tyr
 1               5                  10                  15
Gly Ala Gly Ala Gly Ala Phe Gly Ala Gly Ala Ser Ala Gly Val Gly
             20                  25                  30
Ala Gly Ala Gly Thr Val Ala Gly Tyr Gly Gly Gln Gly Gly Tyr Gly
         35                  40                  45
Ala Gly Ala Gly Ser Ala Gly Gly Tyr Gly Arg Gly Thr Gly Ala Gly
         50                  55                  60
Ala Ala Ala Gly Ala Gly Ala Gly Ala Thr Ala Gly Ala Gly Ala Gly
 65              70                  75                      80
Ala Ala Ala Gly Ala Gly Ala Gly Ala Gly
             85                  90
```

( 2 ) INFORMATION FOR SEQ ID NO:17:

( i ) SEQUENCE CHARACTERISTICS:
        ( A ) LENGTH: 115 amino acids
        ( B ) TYPE: amino acid
        ( D ) TOPOLOGY: linear ( i i ) MOLECULE TYPE: peptide ( v ) FRAGMENT TYPE: C-terminal ( i x ) FEATURE:
        ( A ) NAME/KEY: Peptide
        ( B ) LOCATION: 1..115
        ( D ) OTHER INFORMATION: /label=MISP1C_AA
            / note= "carboxyl terminus of MISP1, see Fig. 4"

( x i ) SEQUENCE DESCRIPTION: SEQ ID NO:17:

```
Asp Lys Glu Ile Ala Cys Trp Ser Arg Cys Arg Tyr Thr Val Ala Ser
 1               5                  10                  15
Thr Thr Ser Arg Leu Ser Ser Ala Glu Ala Ser Ser Arg Ile Ser Ser
             20                  25                  30
Ala Ala Ser Thr Leu Val Ser Gly Gly Tyr Leu Asn Thr Ala Ala Leu
         35                  40                  45
Pro Ser Val Ile Ser Asp Leu Phe Ala Gln Val Gly Ala Ser Ser Pro
     50              55                  60
Val Ile Arg Gln Arg Ser Leu Ile Gln Val Leu Leu Glu Ile Val Ser
 65              70                  75                      80
Ser Leu Ile His Ile Leu Ser Ser Ser Val Gly Trp Val Asp Phe
             85                  90                  95
Ser Ser Val Gly Ser Ser Ala Ala Ala Val Gly Gln Ser Met Gln Val
             100                 105                 110
Val Met Gly
```

(2) INFORMATION FOR SEQ ID NO:18:

(i) SEQUENCE CHARACTERISTICS:
        (A) LENGTH: 116 amino acids
        (B) TYPE: amino acid
        (D) TOPOLOGY: linear (ii) MOLECULE TYPE: peptide (v) FRAGMENT TYPE: C-terminal (ix) FEATURE:
        (A) NAME/KEY: Peptide
        (B) LOCATION: 1..116
        (D) OTHER INFORMATION: /label=MISP2C_AA
            / note= "carboxyl terminus of MISP2, see Fig. 4"

(xi) SEQUENCE DESCRIPTION: SEQ ID NO:18:

```
Gly Gly Tyr Ala Ser Thr Gly Val Gly Ile Gly Ser Thr Val Thr Ser
 1               5                  10                  15

Thr Thr Ser Arg Leu Ser Ser Ala Glu Ala Cys Ser Arg Ile Ser Ala
            20                  25                  30

Ala Ala Ser Thr Leu Val Ser Gly Gly Ser Leu Asn Thr Ala Ala Leu
        35                  40                  45

Pro Ser Val Ile Ser Asp Leu Phe Ala Gln Val Ser Ala Ser Ser Pro
    50                  55                  60

Gly Val Ser Gly Asn Glu Val Leu Ile Gln Val Leu Leu Glu Ile Val
65                  70                  75                  80

Ser Ser Leu Ile His Ile Leu Ser Ser Ser Ser Val Gly Gln Val Asp
                85                  90                  95

Phe Ser Ser Val Gly Ser Ser Ala Ala Ala Val Gly Gln Ser Met Gln
                100                 105                 110

Val Val Met Gly
            115
```

(2) INFORMATION FOR SEQ ID NO:19:

(i) SEQUENCE CHARACTERISTICS:
        (A) LENGTH: 33 amino acids
        (B) TYPE: amino acid
        (D) TOPOLOGY: linear (ii) MOLECULE TYPE: peptide (v) FRAGMENT TYPE: N-terminal (ix) FEATURE:
        (A) NAME/KEY: Peptide
        (B) LOCATION: 1..33
        (D) OTHER INFORMATION: /label=misp1_repeat
            / note= "see Table 1"

(xi) SEQUENCE DESCRIPTION: SEQ ID NO:19:

```
Gly Ala Ala Gly Ala Gly Gly Tyr Gly Arg Gly Ala Gly Gly Tyr Gly
 1               5                  10                  15

Gly Gln Gly Gly Tyr Gly Ala Gly Ala Gly Ala Gly Ala Ala Ala Ala
            20                  25                  30

Ala
```

(2) INFORMATION FOR SEQ ID NO:20:

(i) SEQUENCE CHARACTERISTICS:
        (A) LENGTH: 51 amino acids
        (B) TYPE: amino acid ( D ) TOPOLOGY: linear ( i i ) MOLECULE TYPE: peptide ( v ) FRAGMENT TYPE: internal ( i x ) FEATURE:
  ( A ) NAME/KEY: Peptide
  ( B ) LOCATION: 1..51
  ( D ) OTHER INFORMATION: /label=misp1_repeat
    / note= "see Table 1"

( x i ) SEQUENCE DESCRIPTION: SEQ ID NO:20:

```
Gly Ala Gly Ala Gly Gly Ala Gly Gly Tyr Gly Arg Gly Ala Gly Ala
 1               5                  10                  15
Gly Ala Gly Ala Ala Ala Gly Ala Gly Ala Gly Ala Gly Gly Ala Gly
                20                  25                  30
Tyr Gly Gly Gln Gly Gly Tyr Gly Ala Gly Ala Gly Ala Gly Ala Ala
        35                  40                  45
Ala Ala Ala
        50
```

( 2 ) INFORMATION FOR SEQ ID NO:21:

( i ) SEQUENCE CHARACTERISTICS:
  ( A ) LENGTH: 48 amino acids
  ( B ) TYPE: amino acid
  ( D ) TOPOLOGY: linear ( i i ) MOLECULE TYPE: peptide ( v ) FRAGMENT TYPE: internal ( i x ) FEATURE:
  ( A ) NAME/KEY: Peptide
  ( B ) LOCATION: 1..48
  ( D ) OTHER INFORMATION: /label=misp1_repeat
    / note= "see Table 1"

( x i ) SEQUENCE DESCRIPTION: SEQ ID NO:21:

```
Gly Ala Gly Ala Gly Gly Ala Gly Gly Tyr Gly Arg Gly Ala Gly Ala
 1               5                  10                  15
Gly Ala Gly Ala Ala Ala Gly Ala Gly Ala Gly Gly Tyr Gly Gly Gln
                20                  25                  30
Gly Gly Tyr Gly Ala Gly Ala Gly Ala Gly Ala Ala Ala Ala Ala Ala
        35                  40                  45
```

( 2 ) INFORMATION FOR SEQ ID NO:22:

( i ) SEQUENCE CHARACTERISTICS:
  ( A ) LENGTH: 49 amino acids
  ( B ) TYPE: amino acid
  ( D ) TOPOLOGY: linear ( i i ) MOLECULE TYPE: peptide ( v ) FRAGMENT TYPE: internal ( i x ) FEATURE:
  ( A ) NAME/KEY: Peptide
  ( B ) LOCATION: 1..49
  ( D ) OTHER INFORMATION: /label=misp1_repeat
    / note= "see Table 1"

( x i ) SEQUENCE DESCRIPTION: SEQ ID NO:22:

```
Gly Ala Gly Ser Gly Gly Ala Gly Gly Tyr Gly Arg Gly Ala Gly Ala
 1               5                  10                  15
Gly Ala Gly Ala Ala Ala Gly Ala Gly Ala Gly Ala Gly Ser Tyr Gly
                20                  25                  30
```

-continued

```
Gly Gln Gly Gly Tyr Gly Ala Gly Ala Gly Ala Ala Ala Ala
         35                  40                  45
Ala
```

( 2 ) INFORMATION FOR SEQ ID NO:23:

( i ) SEQUENCE CHARACTERISTICS:
        ( A ) LENGTH: 39 amino acids
        ( B ) TYPE: amino acid
        ( D ) TOPOLOGY: linear ( i i ) MOLECULE TYPE: peptide ( v ) FRAGMENT TYPE: internal ( i x ) FEATURE:
        ( A ) NAME/KEY: Peptide
        ( B ) LOCATION: 1..39
        ( D ) OTHER INFORMATION: /label=misp1_repeat
            / note= "see Table 1"

( x i ) SEQUENCE DESCRIPTION: SEQ ID NO:23:

```
Gly Ala Gly Ala Gly Gly Ala Gly Gly Tyr Gly Arg Gly Ala Gly Ala
1                5                   10                  15
Gly Ala Gly Ala Gly Ala Gly Ala Ala Ala Arg Ala Gly Ala Gly Ala
                 20                  25                  30
Gly Gly Ala Ala Ala Ala Ala
             35
```

( 2 ) INFORMATION FOR SEQ ID NO:24:

( i ) SEQUENCE CHARACTERISTICS:
        ( A ) LENGTH: 47 amino acids
        ( B ) TYPE: amino acid
        ( D ) TOPOLOGY: linear ( i i ) MOLECULE TYPE: peptide ( v ) FRAGMENT TYPE: internal ( i x ) FEATURE:
        ( A ) NAME/KEY: Peptide
        ( B ) LOCATION: 1..47
        ( D ) OTHER INFORMATION: /label=misp1_repeat
            / note= "see Table 1"

( x i ) SEQUENCE DESCRIPTION: SEQ ID NO:24:

```
Gly Ala Gly Ala Gly Gly Ala Gly Gly Tyr Gly Arg Gly Ala Gly Ala
1                5                   10                  15
Gly Ala Gly Ala Ala Ala Gly Ala Gly Ala Gly Ala Gly Gly Tyr Gly
                 20                  25                  30
Gly Gln Ser Gly Tyr Gly Ala Gly Ala Gly Ala Ala Ala Ala Ala
             35                  40                  45
```

( 2 ) INFORMATION FOR SEQ ID NO:25:

( i ) SEQUENCE CHARACTERISTICS:
        ( A ) LENGTH: 55 amino acids
        ( B ) TYPE: amino acid
        ( D ) TOPOLOGY: linear ( i i ) MOLECULE TYPE: peptide ( v ) FRAGMENT TYPE: internal ( i x ) FEATURE:
        ( A ) NAME/KEY: Peptide
        ( B ) LOCATION: 1..55
        ( D ) OTHER INFORMATION: /label=misp1_repeat ( x i ) SEQUENCE DESCRIPTION: SEQ ID NO:25:

```
Gly Ala Gly Ala Gly Gly Ala Gly Gly Tyr Gly Arg Gly Ala Gly Ala
 1               5                       10                  15
Gly Ala Gly Ala Ala Ala Gly Ala Gly Ala Gly Ala Ala Ala Gly Ala
             20                  25                  30
Gly Ala Gly Gly Tyr Gly Gly Gln Gly Gly Tyr Gly Ala Gly Ala Gly
         35                  40                  45
Ala Gly Ala Ala Ala Ala Ala
     50              55
```

( 2 ) INFORMATION FOR SEQ ID NO:26:

( i ) SEQUENCE CHARACTERISTICS:
        ( A ) LENGTH: 47 amino acids
        ( B ) TYPE: amino acid
        ( D ) TOPOLOGY: linear ( i i ) MOLECULE TYPE: peptide ( v ) FRAGMENT TYPE: internal ( i x ) FEATURE:
        ( A ) NAME/KEY: Peptide
        ( B ) LOCATION: 1..47
        ( D ) OTHER INFORMATION: /label=misp1_repeat
        / note= "see Table 1"

( x i ) SEQUENCE DESCRIPTION: SEQ ID NO:26:

```
Gly Ala Gly Ala Gly Gly Ala Gly Gly Tyr Gly Arg Gly Ala Gly Ala
 1               5                       10                  15
Gly Ala Gly Ala Ala Ala Gly Ala Gly Ala Gly Gly Tyr Gly Gly Gln
             20                  25                  30
Gly Gly Tyr Gly Ala Gly Ala Gly Ala Gly Ala Ala Ala Ala Ala
         35                  40                  45
```

( 2 ) INFORMATION FOR SEQ ID NO:27:

( i ) SEQUENCE CHARACTERISTICS:
        ( A ) LENGTH: 50 amino acids
        ( B ) TYPE: amino acid
        ( D ) TOPOLOGY: linear ( i i ) MOLECULE TYPE: peptide ( v ) FRAGMENT TYPE: internal ( i x ) FEATURE:
        ( A ) NAME/KEY: Peptide
        ( B ) LOCATION: 1..50
        ( D ) OTHER INFORMATION: /label=misp1_repeat
        / note= "see Table 1"

( x i ) SEQUENCE DESCRIPTION: SEQ ID NO:27:

```
Thr Gly Ala Gly Gly Ala Gly Gly Tyr Gly Arg Gly Ala Gly Ala Gly
 1               5                       10                  15
Ala Gly Ala Ala Ala Gly Ala Gly Ala Gly Thr Gly Gly Ala Gly Tyr
             20                  25                  30
Gly Gly Gln Gly Gly Tyr Gly Ala Gly Ala Gly Ala Gly Ala Ala Ala
         35                  40                  45
Ala Ala
     50
```

( 2 ) INFORMATION FOR SEQ ID NO:28:

(i) SEQUENCE CHARACTERISTICS:
    (A) LENGTH: 56 amino acids
    (B) TYPE: amino acid
    (D) TOPOLOGY: linear (ii) MOLECULE TYPE: peptide (v) FRAGMENT TYPE: internal (ix) FEATURE:
    (A) NAME/KEY: Peptide
    (B) LOCATION: 1..56
    (D) OTHER INFORMATION: /label=misp1_repeat
        / note= "see Table 1"

(xi) SEQUENCE DESCRIPTION: SEQ ID NO:28:

```
Gly Ala Gly Ala Gly Gly Ala Gly Tyr Gly Arg Gly Ala Gly Ala Gly
 1               5                  10                  15
Ala Gly Ala Ala Ala Gly Ala Gly Ala Gly Ala Ala Ala Gly Ala Gly
                20                  25                  30
Ala Gly Ala Gly Gly Tyr Gly Gly Gln Gly Gly Tyr Gly Ala Gly Ala
                35                  40                  45
Arg Ala Gly Ala Ala Ala Ala Ala
 50                  55
```

(2) INFORMATION FOR SEQ ID NO:29:

(i) SEQUENCE CHARACTERISTICS:
    (A) LENGTH: 54 amino acids
    (B) TYPE: amino acid
    (D) TOPOLOGY: linear (ii) MOLECULE TYPE: peptide (v) FRAGMENT TYPE: internal (ix) FEATURE:
    (A) NAME/KEY: Peptide
    (B) LOCATION: 1..54
    (D) OTHER INFORMATION: /label=misp1_repeat
        / note= "see Table 1"

(xi) SEQUENCE DESCRIPTION: SEQ ID NO:29:

```
Gly Ala Gly Ala Gly Gly Ala Ala Gly Tyr Ser Arg Gly Gly Arg Ala
 1               5                  10                  15
Gly Ala Ala Gly Ala Gly Ala Gly Ala Ala Ala Gly Ala Gly Ala Gly
                20                  25                  30
Ala Gly Gly Tyr Gly Gly Gln Gly Gly Tyr Gly Ala Gly Ala Gly Ala
                35                  40                  45
Gly Ala Ala Ala Ala Ala
 50
```

(2) INFORMATION FOR SEQ ID NO:30:

(i) SEQUENCE CHARACTERISTICS:
    (A) LENGTH: 51 amino acids
    (B) TYPE: amino acid
    (D) TOPOLOGY: linear (ii) MOLECULE TYPE: peptide (v) FRAGMENT TYPE: internal (ix) FEATURE:
    (A) NAME/KEY: Peptide
    (B) LOCATION: 1..51
    (D) OTHER INFORMATION: /label=misp1_repeat
        / note= "see Table 1"

(xi) SEQUENCE DESCRIPTION: SEQ ID NO:30:

Gly Ala Gly Ser Gly Gly Ala Gly Gly Tyr Gly Arg Gly Ala Gly Ala
1               5                   10                  15

Gly Ala Ala Ala Gly Ala Gly Ala Ala Gly Ala Gly Ala Ala Gly Ala
                20                  25                  30

Gly Gly Tyr Gly Gly Gln Gly Gly Tyr Gly Ala Gly Ala Gly Ala Ala
            35                  40                  45

Ala Ala Ala
        50

( 2 ) INFORMATION FOR SEQ ID NO:31:

( i ) SEQUENCE CHARACTERISTICS:
        ( A ) LENGTH: 36 amino acids
        ( B ) TYPE: amino acid
        ( D ) TOPOLOGY: linear ( i i ) MOLECULE TYPE: peptide ( v ) FRAGMENT TYPE: C-terminal ( i x ) FEATURE:
        ( A ) NAME/KEY: Peptide
        ( B ) LOCATION: 1..36
        ( D ) OTHER INFORMATION: /label=misp1_repeat
            / note= "see Table 1"

( x i ) SEQUENCE DESCRIPTION: SEQ ID NO:31:

Gly Ala Gly Ala Gly Arg Gly Gly Tyr Gly Arg Gly Ala Gly Ala Gly
1               5                   10                  15

Gly Tyr Gly Gly Gln Gly Gly Tyr Gly Ala Gly Ala Gly Ala Gly Ala
                20                  25                  30

Ala Ala Ala Ala
        35

( 2 ) INFORMATION FOR SEQ ID NO:32:

( i ) SEQUENCE CHARACTERISTICS:
        ( A ) LENGTH: 55 amino acids
        ( B ) TYPE: amino acid
        ( D ) TOPOLOGY: linear ( i i ) MOLECULE TYPE: peptide ( v ) FRAGMENT TYPE: internal ( i x ) FEATURE:
        ( A ) NAME/KEY: Peptide
        ( B ) LOCATION: 1..55
        ( D ) OTHER INFORMATION: /label=misp1_repeat
            / note= "consensus sequence of MiSP1 repeats"

( x i ) SEQUENCE DESCRIPTION: SEQ ID NO:32:

Arg Gly Ala Ala Gly Ala Ala Gly Ala Gly Ala Gly Ala Ala Ala Gly
1               5                   10                  15

Ala Gly Ala Gly Ala Gly Ala Gly Gly Tyr Gly Gly Gln Gly Gly Tyr
                20                  25                  30

Gly Ala Gly Ala Gly Ala Gly Ala Ala Ala Ala Ala Gly Ala Gly Ala
            35                  40                  45

Gly Gly Ala Gly Gly Tyr Gly
        50              55

( 2 ) INFORMATION FOR SEQ ID NO:33:

( i ) SEQUENCE CHARACTERISTICS:
        ( A ) LENGTH: 11 amino acids
        ( B ) TYPE: amino acid (D) TOPOLOGY: linear (ii) MOLECULE TYPE: peptide (v) FRAGMENT TYPE: internal (ix) FEATURE:
    (A) NAME/KEY: Peptide
    (B) LOCATION: 1..11
    (D) OTHER INFORMATION: /label=misp1_generic
        / note= "generic formula for MiSP1"

(ix) FEATURE:
    (A) NAME/KEY: Duplication
    (B) LOCATION: 3..4
    (D) OTHER INFORMATION: /label=GA
        / note= "(GA) repeated 1 to 6 times"

(ix) FEATURE:
    (A) NAME/KEY: Duplication
    (B) LOCATION: 5
    (D) OTHER INFORMATION: /label=A
        / note= "present as 0 to 4 residues"

(ix) FEATURE:
    (A) NAME/KEY: Duplication
    (B) LOCATION: 6..8
    (D) OTHER INFORMATION: /label=GGX
        / note= "X is tyrosine, glutamine or alanine; unit
        is repeated 1 to 4 times."

(ix) FEATURE:
    (A) NAME/KEY: Duplication
    (B) LOCATION: 9..10
    (D) OTHER INFORMATION: /label=GA
        / note= "repeated 1 to 6 times"

(ix) FEATURE:
    (A) NAME/KEY: Duplication
    (B) LOCATION: 11
    (D) OTHER INFORMATION: /label=A
        / note= "present as 0 to 4 residues"

(xi) SEQUENCE DESCRIPTION: SEQ ID NO:33:

```
Gly Arg Gly Ala Ala Gly Gly Xaa Gly Ala Ala
 1               5                   10
```

(2) INFORMATION FOR SEQ ID NO:34:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (v) FRAGMENT TYPE: internal (ix) FEATURE:
        (A) NAME/KEY: Peptide
        (B) LOCATION: 1..15
        (D) OTHER INFORMATION: /label=MaSP1_generic
            / note= "generic formula for MaSP1 protein (major
            ampullate spider silk protein)."

(ix) FEATURE:
        (A) NAME/KEY: Duplication
        (B) LOCATION: 1..3
        (D) OTHER INFORMATION: /label=XGG
            / note= "X is tyrosine or glutamine; unit is
            repeated 2 to 3 times"

(ix) FEATURE:
        (A) NAME/KEY: Region
        (B) LOCATION: 4..6
        (D) OTHER INFORMATION: /label=XGA
            / note= "X is tyrosine or glutamine; unit is
            present once."

( i x ) FEATURE:
  ( A ) NAME/KEY: Duplication
  ( B ) LOCATION: 7..9
  ( D ) OTHER INFORMATION: /label=GXG
    / note= "X is tyrosine or glutamine; unit is repeated 1 to three times."

( i x ) FEATURE:
  ( A ) NAME/KEY: Duplication
  ( B ) LOCATION: 10..12
  ( D ) OTHER INFORMATION: /label=AGA
    / note= "unit is repeated 5 to 7 times"

( i x ) FEATURE:
  ( A ) NAME/KEY: Duplication
  ( B ) LOCATION: 13
  ( D ) OTHER INFORMATION: /label=G
    / note= "present as 1 or 2 residues"

( x i ) SEQUENCE DESCRIPTION: SEQ ID NO:34:

```
Xaa Gly Gly Xaa Gly Ala Gly Xaa Gly Ala Gly Ala Gly Ala Gly
 1               5                  10                  15
```

( 2 ) INFORMATION FOR SEQ ID NO:35:

( i ) SEQUENCE CHARACTERISTICS:
    ( A ) LENGTH: 14 amino acids
    ( B ) TYPE: amino acid
    ( D ) TOPOLOGY: linear ( i i ) MOLECULE TYPE: peptide ( v ) FRAGMENT TYPE: internal ( i x ) FEATURE:
    ( A ) NAME/KEY: Peptide
    ( B ) LOCATION: 1..14
    ( D ) OTHER INFORMATION: /label=MaSP2_generic
      / note= "generic formula for MaSP2 protein (major ampullate spider silk protein)."

( i x ) FEATURE:
    ( A ) NAME/KEY: Duplication
    ( B ) LOCATION: 1..10
    ( D ) OTHER INFORMATION: /label=GPG2YGPGQ2
      / note= "unit is repeated 2 or 3 times"

( i x ) FEATURE:
    ( A ) NAME/KEY: Duplication
    ( B ) LOCATION: 11..12
    ( D ) OTHER INFORMATION: /label=XX
      / note= "X is GPG or GPS"

( i x ) FEATURE:
    ( A ) NAME/KEY: Duplication
    ( B ) LOCATION: 14
    ( D ) OTHER INFORMATION: /label=A
      / note= "present as 7 to 10 residues"

( x i ) SEQUENCE DESCRIPTION: SEQ ID NO:35:

```
Gly Pro Gly Gly Tyr Gly Pro Gly Gln Gln Xaa Xaa Ser Ala
 1               5                  10
```

( 2 ) INFORMATION FOR SEQ ID NO:36:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: peptide ( v ) FRAGMENT TYPE: internal ( i x ) FEATURE:

( A ) NAME/KEY: Peptide
( B ) LOCATION: 1..6
( D ) OTHER INFORMATION: /label=MiSP_simple
/ note= "simplified MiSP1 generic formula; x is tyrosine, glutamine or alan..."

( i x ) FEATURE:
( A ) NAME/KEY: Duplication
( B ) LOCATION: 1..3
( D ) OTHER INFORMATION: /label=GGX
/ note= "X is tyrosine, glutamine or alanine; unit is repeated 1 to 4 times."

( i x ) FEATURE:
( A ) NAME/KEY: Duplication
( B ) LOCATION: 4..5
( D ) OTHER INFORMATION: /label=GA
/ note= "unit is present 0 to 4 times"

( i x ) FEATURE:
( A ) NAME/KEY: Duplication
( B ) LOCATION: 6
( D ) OTHER INFORMATION: /label=A
/ note= "present as 1 to 6 residues"

( x i ) SEQUENCE DESCRIPTION: SEQ ID NO:36:

Gly Gly Xaa Gly Ala Ala
1               5

( 2 ) INFORMATION FOR SEQ ID NO:37:

( i ) SEQUENCE CHARACTERISTICS:
( A ) LENGTH: 47 amino acids
( B ) TYPE: amino acid
( D ) TOPOLOGY: linear ( i i ) MOLECULE TYPE: peptide ( v ) FRAGMENT TYPE: N-terminal ( i x ) FEATURE:
( A ) NAME/KEY: Peptide
( B ) LOCATION: 1..47
( D ) OTHER INFORMATION: /label=MaSP2_repeat
/ note= "see Table 2"

( x i ) SEQUENCE DESCRIPTION: SEQ ID NO:37:

Gly Pro Gly Gln Gln Gly Pro Gly Gly Tyr Gly Pro Gly Gln Gln Gly
1               5                   10                  15

Pro Ser Gly Pro Gly Ser Ala Ala Ala Ala Ala Ala Ala Ala Ala Ala
                20                  25                  30

Gly Pro Gly Gly Tyr Gly Pro Gly Gln Gln Gly Pro Gly Gly Tyr
            35                  40                  45

( 2 ) INFORMATION FOR SEQ ID NO:38:

( i ) SEQUENCE CHARACTERISTICS:
( A ) LENGTH: 38 amino acids
( B ) TYPE: amino acid
( D ) TOPOLOGY: linear ( i i ) MOLECULE TYPE: peptide ( v ) FRAGMENT TYPE: internal ( i x ) FEATURE:
( A ) NAME/KEY: Peptide
( B ) LOCATION: 1..38
( D ) OTHER INFORMATION: /label=MaSP2_repeat
/ note= "see Table 2"

( x i ) SEQUENCE DESCRIPTION: SEQ ID NO:38:

Gly Pro Gly Gln Gln Gly Pro Gly Arg Tyr Gly Pro Gly Gln Gln Gly

```
                1               5                      10                       15
            Pro Ser Gly Pro Gly Ser Ala Ala Ala Ala Ala Ala Gly Ser Gly Gln
                            20                  25                  30

Gln Gly Pro Gly Gly Tyr
                        35
```

( 2 ) INFORMATION FOR SEQ ID NO:39:

( i ) SEQUENCE CHARACTERISTICS:
        ( A ) LENGTH: 52 amino acids
        ( B ) TYPE: amino acid
        ( D ) TOPOLOGY: linear ( i i ) MOLECULE TYPE: peptide ( v ) FRAGMENT TYPE: internal ( i x ) FEATURE:
        ( A ) NAME/KEY: Peptide
        ( B ) LOCATION: 1..52
        ( D ) OTHER INFORMATION: /label=MaSP2_repeat
             / note= "see Table 2"

( x i ) SEQUENCE DESCRIPTION: SEQ ID NO:39:

```
            Gly Pro Arg Gln Gln Gly Pro Gly Gly Tyr Gly Gln Gly Gln Gln Gly
            1               5                      10                      15

Pro Ser Gly Pro Gly Ser Ala Ala Ala Ala Ser Ala Ala Ala Ser Ala
                            20                  25                  30

Glu Ser Gly Gln Gln Gly Pro Gly Gly Tyr Gly Pro Gly Gln Gln Gly
                        35                  40                  45

Pro Gly Gly Tyr
                    50
```

( 2 ) INFORMATION FOR SEQ ID NO:40:

( i ) SEQUENCE CHARACTERISTICS:
        ( A ) LENGTH: 40 amino acids
        ( B ) TYPE: amino acid
        ( D ) TOPOLOGY: linear ( i i ) MOLECULE TYPE: peptide ( v ) FRAGMENT TYPE: internal ( i x ) FEATURE:
        ( A ) NAME/KEY: Peptide
        ( B ) LOCATION: 1..40
        ( D ) OTHER INFORMATION: /label=MaSP2_repeat
             / note= "see Table 2"

( x i ) SEQUENCE DESCRIPTION: SEQ ID NO:40:

```
            Gly Pro Gly Gln Gln Gly Pro Gly Gly Tyr Gly Pro Gly Gln Gln Gly
            1               5                      10                      15

Pro Ser Gly Pro Gly Ser Ala Ala Ala Ala Ala Ala Ala Ser Gly Pro
                            20                  25                  30

Gly Gln Gln Gly Pro Gly Gly Tyr
                        35                  40
```

( 2 ) INFORMATION FOR SEQ ID NO:41:

( i ) SEQUENCE CHARACTERISTICS:
        ( A ) LENGTH: 41 amino acids
        ( B ) TYPE: amino acid
        ( D ) TOPOLOGY: linear ( i i ) MOLECULE TYPE: peptide ( v ) FRAGMENT TYPE: internal ( i x ) FEATURE:
  ( A ) NAME/KEY: Peptide
  ( B ) LOCATION: 1..41
  ( D ) OTHER INFORMATION: /label=MaSP2_repeat
    / note= "see Table 2"

( x i ) SEQUENCE DESCRIPTION: SEQ ID NO:41:

Gly Pro Gly Gln Gln Gly Pro Gly Gly Tyr Gly Pro Gly Gln Gln Gly
1               5                   10                  15

Pro Ser Gly Pro Gly Ser Ala Ala Ala Ala Ala Ala Ala Ala Ser Gly
            20                  25                  30

Pro Gly Gln Gln Gly Pro Gly Gly Tyr
        35                  40

( 2 ) INFORMATION FOR SEQ ID NO:42:

( i ) SEQUENCE CHARACTERISTICS:
    ( A ) LENGTH: 29 amino acids
    ( B ) TYPE: amino acid
    ( D ) TOPOLOGY: linear ( i i ) MOLECULE TYPE: peptide ( v ) FRAGMENT TYPE: internal ( i x ) FEATURE:
    ( A ) NAME/KEY: Peptide
    ( B ) LOCATION: 1..29
    ( D ) OTHER INFORMATION: /label=MaSP2_repeat
      / note= "see Table 2"

( x i ) SEQUENCE DESCRIPTION: SEQ ID NO:42:

Gly Pro Gly Gln Gln Gly Pro Gly Gly Tyr Gly Pro Gly Gln Gln Gly
1               5                   10                  15

Leu Ser Gly Pro Gly Ser Ala Ala Ala Ala Ala Ala Ala
            20                  25

( 2 ) INFORMATION FOR SEQ ID NO:43:

( i ) SEQUENCE CHARACTERISTICS:
    ( A ) LENGTH: 36 amino acids
    ( B ) TYPE: amino acid
    ( D ) TOPOLOGY: linear ( i i ) MOLECULE TYPE: peptide ( v ) FRAGMENT TYPE: internal ( i x ) FEATURE:
    ( A ) NAME/KEY: Peptide
    ( B ) LOCATION: 1..36
    ( D ) OTHER INFORMATION: /label=MaSP2_repeat
      / note= "see Table 2"

( x i ) SEQUENCE DESCRIPTION: SEQ ID NO:43:

Gly Pro Gly Gln Gln Gly Pro Gly Gly Tyr Gly Pro Gly Gln Gln Gly
1               5                   10                  15

Pro Ser Gly Pro Gly Ser Ala Ala Ala Ala Ala Ala Ala Ala Ala Gly
            20                  25                  30

Pro Gly Gly Tyr
        35

( 2 ) INFORMATION FOR SEQ ID NO:44:

( i ) SEQUENCE CHARACTERISTICS:
    ( A ) LENGTH: 39 amino acids
    ( B ) TYPE: amino acid
    ( D ) TOPOLOGY: linear ( i i ) MOLECULE TYPE: peptide ( v ) FRAGMENT TYPE: internal ( i x ) FEATURE:
    ( A ) NAME/KEY: Peptide
    ( B ) LOCATION: 1..39
    ( D ) OTHER INFORMATION: /label=MaSP2_repeat
        / note= "see Table 2"

( x i ) SEQUENCE DESCRIPTION: SEQ ID NO:44:

```
Gly Pro Gly Gln Gln Gly Pro Gly Gly Tyr Gly Pro Gly Gln Gln Gly
 1               5                  10                  15

Pro Ser Gly Ala Gly Ser Ala Ala Ala Ala Ala Ala Ala Gly Pro Gly
                20                  25                  30

Gln Gln Gly Leu Gly Gly Tyr
            35
```

( 2 ) INFORMATION FOR SEQ ID NO:45:

( i ) SEQUENCE CHARACTERISTICS:
        ( A ) LENGTH: 32 amino acids
        ( B ) TYPE: amino acid
        ( D ) TOPOLOGY: linear ( i i ) MOLECULE TYPE: peptide ( v ) FRAGMENT TYPE: internal ( i x ) FEATURE:
        ( A ) NAME/KEY: Peptide
        ( B ) LOCATION: 1..32
        ( D ) OTHER INFORMATION: /label=MaSP2_repeat
            / note= "see Table 2"

( x i ) SEQUENCE DESCRIPTION: SEQ ID NO:45:

```
Gly Pro Gly Gln Gln Gly Pro Gly Gly Tyr Gly Pro Gly Gln Gln Gly
 1               5                  10                  15

Pro Gly Gly Tyr Gly Pro Gly Ser Ala Ser Ala Ala Ala Ala Ala Ala
                20                  25                  30
```

( 2 ) INFORMATION FOR SEQ ID NO:46:

( i ) SEQUENCE CHARACTERISTICS:
        ( A ) LENGTH: 37 amino acids
        ( B ) TYPE: amino acid
        ( D ) TOPOLOGY: linear ( i i ) MOLECULE TYPE: peptide ( v ) FRAGMENT TYPE: internal ( i x ) FEATURE:
        ( A ) NAME/KEY: Peptide
        ( B ) LOCATION: 1..37
        ( D ) OTHER INFORMATION: /label=MaSP2_repeat
            / note= "see Table 2"

( x i ) SEQUENCE DESCRIPTION: SEQ ID NO:46:

```
Gly Pro Gly Gln Gln Gly Pro Gly Gly Tyr Gly Pro Gly Gln Gln Gly
 1               5                  10                  15

Pro Ser Gly Pro Gly Ser Ala Ser Ala Ala Ala Ala Ala Ala Ala Ala
                20                  25                  30

Gly Pro Gly Gly Tyr
            35
```

( 2 ) INFORMATION FOR SEQ ID NO:47:

( i ) SEQUENCE CHARACTERISTICS:
: ( A ) LENGTH: 37 amino acids
: ( B ) TYPE: amino acid
: ( D ) TOPOLOGY: linear ( i i ) MOLECULE TYPE: peptide ( v ) FRAGMENT TYPE: internal ( i x ) FEATURE:
: ( A ) NAME/KEY: Peptide
: ( B ) LOCATION: 1..37
: ( D ) OTHER INFORMATION: /label=MaSP2_repeat
:   / note= "see Table 2"

( x i ) SEQUENCE DESCRIPTION: SEQ ID NO:47:

```
Gly Pro Gly Gln Gln Gly Pro Gly Gly Tyr Ala Pro Gly Gln Gln Gly
 1               5                  10                  15
Pro Ser Gly Pro Gly Ser Ala Ser Ala Ala Ala Ala Ala Ala Ala Ala
                20                  25                  30
Gly Pro Gly Gly Tyr
                35
```

( 2 ) INFORMATION FOR SEQ ID NO:48:

( i ) SEQUENCE CHARACTERISTICS:
: ( A ) LENGTH: 36 amino acids
: ( B ) TYPE: amino acid
: ( D ) TOPOLOGY: linear ( i i ) MOLECULE TYPE: peptide ( v ) FRAGMENT TYPE: C-terminal ( i x ) FEATURE:
: ( A ) NAME/KEY: Peptide
: ( B ) LOCATION: 1..36
: ( D ) OTHER INFORMATION: /label=MaSP2_repeat
:   / note= "see Table 2"

( x i ) SEQUENCE DESCRIPTION: SEQ ID NO:48:

```
Gly Pro Gly Gln Gln Gly Pro Gly Gly Tyr Ala Pro Gly Gln Gln Gly
 1               5                  10                  15
Pro Ser Gly Pro Gly Ser Ala Ala Ala Ala Ala Ala Ala Ser Ala Gly
                20                  25                  30
Pro Gly Gly Tyr
                35
```

( 2 ) INFORMATION FOR SEQ ID NO:49:

( i ) SEQUENCE CHARACTERISTICS:
: ( A ) LENGTH: 37 amino acids
: ( B ) TYPE: amino acid
: ( D ) TOPOLOGY: linear ( i i ) MOLECULE TYPE: peptide ( v ) FRAGMENT TYPE: internal ( i x ) FEATURE:
: ( A ) NAME/KEY: Peptide
: ( B ) LOCATION: 1..37
: ( D ) OTHER INFORMATION: /label=MaSP2_consensus
:   / note= "consensus sequence of MaSP2 repeat units"

( x i ) SEQUENCE DESCRIPTION: SEQ ID NO:49:

```
Gly Pro Gly Gln Gln Gly Pro Gly Gly Tyr Gly Pro Gly Gln Gln Gly
 1               5                  10                  15
Pro Ser Gly Pro Gly Ser Ala Ala Ala Ala Ala Ala Ala Ala Ala Ala
                20                  25                  30
```

```
          Gly  Pro  Gly  Gly  Tyr
                         35
```

( 2 ) INFORMATION FOR SEQ ID NO:50:

( i ) SEQUENCE CHARACTERISTICS:
        ( A ) LENGTH: 84 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i x ) FEATURE:
        ( A ) NAME/KEY: -
        ( B ) LOCATION: 1..84
        ( D ) OTHER INFORMATION: /label=oligonucleotide
            / note= "S2 long oligo"

( x i ) SEQUENCE DESCRIPTION: SEQ ID NO:50:

```
TCTAGCCCGG GTGGCTATGG TCCTGGACAG CAAGGTCCTG GCGGTTACGG TCCTGGCCAA      60

CAGGGTCCCT CTGGTCCAGG CAGT                                            84
```

( 2 ) INFORMATION FOR SEQ ID NO:51:

( i ) SEQUENCE CHARACTERISTICS:
        ( A ) LENGTH: 59 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: -
        ( B ) LOCATION: 1..59
        ( D ) OTHER INFORMATION: /label=oligonucleotide
            / note= "S2 short oligo"

( x i ) SEQUENCE DESCRIPTION: SEQ ID NO:51:

```
TCCGGACCTG CTGCGGCGGC TGCGGCAGCT GCACTGCCTG GACCAGAGGG ACCCTGTTG      59
```

( 2 ) INFORMATION FOR SEQ ID NO:52:

( i ) SEQUENCE CHARACTERISTICS:
        ( A ) LENGTH: 35 amino acids
        ( B ) TYPE: amino acid
        ( D ) TOPOLOGY: linear ( i i ) MOLECULE TYPE: peptide ( v ) FRAGMENT TYPE: internal ( i x ) FEATURE:
        ( A ) NAME/KEY: Peptide
        ( B ) LOCATION: 1..35
        ( D ) OTHER INFORMATION: /label=MaSP2_repeat
            / note= "basic repeat unit of MaSP2 protein"

( x i ) SEQUENCE DESCRIPTION: SEQ ID NO:52:

```
Pro  Gly  Gly  Tyr  Gly  Pro  Gly  Gln  Gln  Gly  Pro  Gly  Gly  Tyr  Gly  Pro
 1                   5                        10                       15

Gly  Gln  Gln  Gly  Pro  Ser  Gly  Pro  Gly  Ser  Ala  Ala  Ala  Ala  Ala  Ala
                20                        25                       30

Ala  Ala  Gly
          35
```

( 2 ) INFORMATION FOR SEQ ID NO:53:

( i ) SEQUENCE CHARACTERISTICS:
        ( A ) LENGTH: 13 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i x ) FEATURE:
        ( A ) NAME/KEY: -
        ( B ) LOCATION: 1..13
        ( D ) OTHER INFORMATION: /label=enzyme_site
            / note= "generic recognition site for Sfi I
            restriction enzyme"

( x i ) SEQUENCE DESCRIPTION: SEQ ID NO:53:

GGCCNNNNNG GCC                                              13

( 2 ) INFORMATION FOR SEQ ID NO:54:

( i ) SEQUENCE CHARACTERISTICS:
        ( A ) LENGTH: 13 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: -
        ( B ) LOCATION: 1..13
        ( D ) OTHER INFORMATION: /label=Sfi_I_site
            / note= "top strand of synthetic Sfi I/AlwN I
            linker"

( x i ) SEQUENCE DESCRIPTION: SEQ ID NO:54:

GGCCGCAGCG GCC                                             13

( 2 ) INFORMATION FOR SEQ ID NO:55:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( v ) FRAGMENT TYPE: internal ( i x ) FEATURE:
        ( A ) NAME/KEY: Peptide
        ( B ) LOCATION: 1..4
        ( D ) OTHER INFORMATION: /label=linker_peptide
            / note= "amino acids encoded by Sfi I/AlwN I
            linker"

( x i ) SEQUENCE DESCRIPTION: SEQ ID NO:55:

Ala Ala Ala Ala
1

( 2 ) INFORMATION FOR SEQ ID NO:56:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( v ) FRAGMENT TYPE: internal

```
( i x ) FEATURE:
    ( A ) NAME/KEY: Peptide
    ( B ) LOCATION: 1..6
    ( D ) OTHER INFORMATION: /label=NBS_peptides
        / note= "see discussion page 13"

( x i ) SEQUENCE DESCRIPTION: SEQ ID NO:56:

Gly  Gly  Gln  Gly  Gly  Tyr
1                 5
```

CDNAS ENCODING MINOR AMPULLATE SPIDER SILK PROTEINS

RELATED APPLICATIONS

The present application is related to copending application U.S. Ser. No. 07/684,819, filed Apr. 15, 1991, the entire contents of which are hereby incorporated by reference.

FIELD OF THE INVENTION

The present invention relates to polypeptides that form macroscopic fibers and to cloned DNA encoding such polypeptides. The proteins are some of those which constitute silks made by spiders. Preferred embodiments of the present invention are those silk proteins made in the minor ampullate glands of the spider *Nephila clavipes*. The silks of the present invention also encompass fibers made from synthetic polypeptides of amino acid sequences derivable from the amino acid sequence of the *N. clavipes* ampullate late silks or made from polypeptides expressed from cloned DNA obtained from a library of spider complementary or genomic DNA.

BACKGROUND OF THE INVENTION

The orb web spiders (Nephila) possess six types of silk synthetic glands, two of which are the major and minor ampullate organs. The major and minor ampullate silks are distinguishable by their physical and chemical properties.

The major ampullate (dragline) silk possesses unique physical properties, combining high tensile strength and substantial elasticity [Denny, M. W. *J. Exp. Biol.*, 65, 483–506 (1976); Lucas, F. *Discovery*, 25, 20–26 (1964)]. Previous investigations suggest that spider silk is composed of a single large protein, primarily containing pseudo-crystalline regions of stack β-pleated sheet alternating with amorphous domains, [Warwicker, J. O., *J. Mol. Biol.*, 2, 350–362 (1960); Lucase, F. et al, *J. Text inst.*, 46, T440–T452 (1985); Hepburn, H. R. et al., *Insect Biochem.*, 9, 69–71 (1979)].

In fact, the major ampullate silk of *Nephila clavipes* was found to be composed of a composite of two proteins. cDNA clones encoding both of the proteins comprising the major ampullate silk are described in copending application U.S. Ser. No. 07/684,819. We describe herein the isolation and characterization of cDNA clones encoding proteins composing minor ampullate silk.

SUMMARY OF THE INVENTION

Spider silk is composed of fibers formed from proteins. We have found that natural spider silk fibers are composites of two or more proteins. However, it is possible to form fibers from a single spider silk protein. In general, spider silk proteins are found to have primary amino acid sequences that can be characterized as indirect repeats of a short consensus sequence. Variation in the consensus sequence is then responsible for the distinguishable properties of the different silk proteins.

Furthermore, silk fibers can be made from synthetic polypeptides having amino acid sequences substantially similar to the consensus repeat unit of a silk protein or from polypeptides expressed from cloned DNA encoding a natural or engineered silk protein.

Thus, it is one object of the present invention to provide cloned DNA which encodes a spider silk protein. The cloned DNA is preferably obtained from an orb web spider (Nephila). Cloned cDNA from the minor ampullate late gland of *Nephila clavipes* is described in detail below.

Naturally occurring spider silk proteins have an imperfectly repetitive structure. However, the imperfection in the repetition is likely to be a consequence of the process by which the silk protein genes evolved, rather than a requirement for fiber formation. The imperfection in repetition is thus likely to only subtly affect the characteristics of the fibers which form from the aggregation of the protein molecules. Accordingly, it is a second object of the present invention to provide cloned DNA encoding an engineered spider silk protein comprising a polypeptide having direct repeats of a unit amino acid sequence. Alternatively, the cDNA may include several different unit amino acid sequences to form a "copolymer" silk protein.

It is a third object of the invention to provide a spider silk protein expressed from a cloned DNA, wherein the cloned DNA is either one obtained from a spider ampullate gland cDNA, a genomic DNA, or synthetic DNA.

Finally, it is an additional object of the present invention to provide fibers made from silk protein obtained by expression of cloned DNA.

BRIEF DESCRIPTION OF THE DRAWINGS

FIGS. 1A–1F shows the nucleotide and the amino acid sequence translation of the insert from pMISS1 (SEQ. ID. NOS.:1 and 2).

FIG. 2A–2D shows the nucleotide and the amino acid sequence translation of the portions of the insert from pMISS2 that have been sequenced. 2A shows 309 nucleotides at the 5' end of pMISS2 (SEQ. ID. NO.:3). 2B shows 165 nucleotides of the PstI fragment 4 (see FIG. 4, SEQ. ID. NO.:5). 2C, 2D show the 870 nucleotides at the 3' end of the insert in pMISS2 (SEQ. ID. NO.:7).

FIGS. 3A–3C shows the nucleotide and the amino acid sequence translation of the portions of the inserts from the 11-1 and 11-2 clones (pMISS3) that have been sequenced. 3A shows 165 nucleotides from the forward primer of the 11-1 clone SEQ. ID. NOS.:9–10). 3B shows 240 nucleotides from the reverse primer of the 11-1 clone (SEQ. ID. NOS.:11–12). 3C shows 146 nucleotides from the forward primer of the 11-2 clone (SEQ. ID. NOS.:13–14).

FIG. 4 shows the alignment of the amino acid sequences of the nonrepetitive regions of MiSP1 and MiSP2 (SEQ. ID. NOS.:15–18).

DETAILED DESCRIPTION OF THE INVENTION

Figure 5:
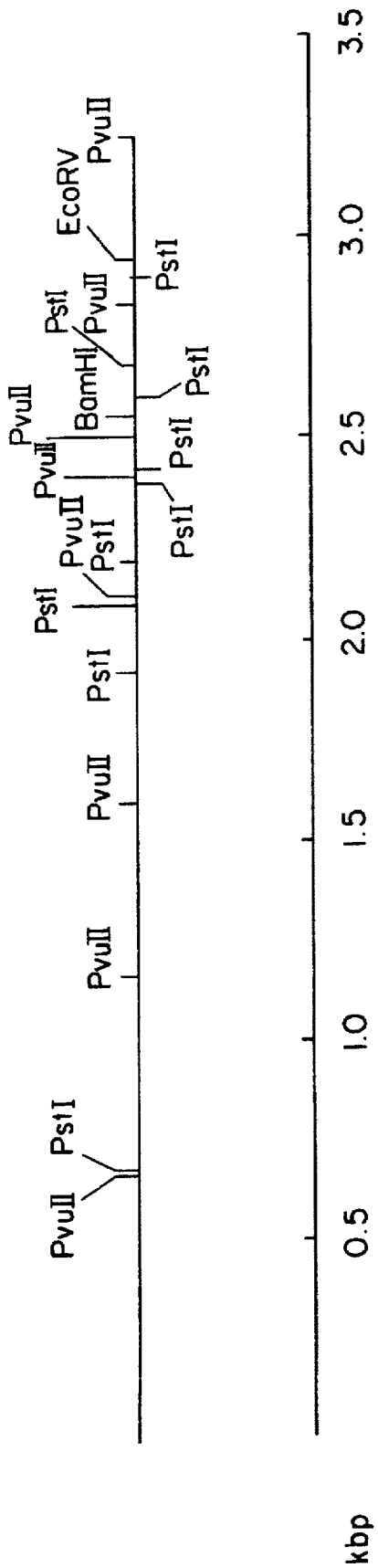
FIG. 5 shows a restriction map of the pMISS1 insert cDNA.

Studies in our laboratory have established that the major ampullate silk is composed of two distinct proteins. The major ampullate silk proteins possess the secondary structure predicted by Warwicker and others. The primary structure of the major ampullate silk proteins is characterized by indirect repeat of a discrete repeat unit. The sequence of the repeat unit is different for each of the proteins comprising the major ampullate silk.

The Nephila minor ampullate silk can be distinguished from the Nephila major ampullate silk by both physical and chemical properties. In contrast to the elasticity exhibited by the major ampullate silk, the minor ampullate silk is observed to yield without recoil. The minor silk will stretch about 25% of its initial length before breaking, exhibiting a tensile strength of nearly 100,000 psi. The amino acid composition of solubilized minor ampullate silk also differs from that of solubilized major ampullate silk.

Like the major ampullate silk proteins (major spidroin 1, MaSP1; major spidroin 2, MaSP2), the proteins comprising minor ampullate silk are found to have a primary structure dominated by imperfect repetition of a short sequence of amino acids. A "unit repeat" constitutes one such short sequence. Thus, the primary structure of the spider silk proteins is considered to consist mostly of a series of small variations of a unit repeat. The unit repeats in the naturally occurring proteins are often distinct from each other. That is, there is little or no exact duplication of the unit repeats along the length of the protein. However, synthetic spider silks can be made wherein the primary structure of the protein can be described as a number of exact repetitions of a single unit repeat. Additional synthetic spider silks can be described as a number of repetitions of one unit repeat together with a number of repetitions of a second unit repeat. Such a structure would be similar to a typical block copolymer. Of course, unit repeats of several different sequences can also be combined.

Spider Silk Protein 1 and spider Silk Protein 2 may each have 900 to 2700 amino acids with 25 to 100, preferably 30 to 90 repeats. The spider silk or fragment or variant thereof usually has a molecular weight of at least about 16,000 daltons, preferably 16,000 to 100,000 daltons, more preferably 50,000 to 80,000 daltons for fragments and greater than 100,000 but less than 300,000 daltons, preferably 120,000 to 300,000 daltons for the full length protein.

An alternative way to describe the primary structure of spider silk proteins is to consider a "consensus" sequence that is derived from an alignment of the unit repeats. Such a consensus sequence is the length of most of the unit repeats and accounts for the variation at each position of the unit repeat by including the residue most common at each position. For the MaSP2 protein, the consensus sequence derived is GPGQQGPGGYGPGQQGPSGPG-SAAAAAAAAAAGPGGY (SEQ. ID. NO.:49) (Table 2).

Cloned DNA of the present invention includes sequences shown in FIGS. 1A–1F, 2A–2C and 3A–3C. The cloned DNA of the present invention also includes DNA molecules made from Nephila DNA or RNA templates by PCR or the like, using primers made from sequences shown in FIGS. 1A–1F, 2A–2C and 3A–3C. Finally, cloned DNA of the present invention also encompasses polynucleotides which can hybridize to DNA having sequences shown in FIGS. 1A–1F, 2A–2C and 3A–3C under hybridization conditions typically used for library screening and Southern blotting. Preferably such hybridization conditions are those obtained by a solution of 6X SSC or SSPE, 5X Denhardt's solution, 0.5% SDS at a temperature of about 68° C., or those obtained by the same solution that is also 50% in formamide at a temperature of about 42° C. Alternatively, the hybridization conditions are those wherein the temperature is about 15°–20° C. below the $T_m$ calculated for the solution conditions. [See, J. Sambrook et al., *Molecular Cloning: A Laboratory Manual*, 2nd ed., pp. 9.47–9.58, c. 1989 by Cold Spring Harbor Laboratory Press, Cold Spring Harbor, N.Y.].

The polypeptides of the present invention can be made by direct synthesis or by expression from cloned DNA. The means for expressing cloned DNA are generally known in the art. However, there are some considerations for design of expression vectors that are unusual for expressing DNA encoding the spider silk proteins of the present invention.

First, the proteins are highly repetitive in their structure. Accordingly, cloned DNA should be propagated and expressed in host cell strains that will maintain repetitive sequences in extrachromosomal elements (e.g. SURE™ cells, Stratagene). Also, due to the high content of alanine, glycine, proline, and glutamine, it might be advantageous to use a host cell which overexpresses tRNA for these amino acids.

The proteins of the present invention can otherwise be expressed using vectors providing for high level transcription, fusion proteins allowing affinity purification through an epitope tag, and the like. The hosts can be either bacterial or eukaryotic. It is considered that yeast, especially *Saccharomyces cerevisisae*, or insect cells might be advantageous eukaryotic hosts.

Fibrillar aggregates will form by spontaneous self-assembly of spider silk proteins when the protein concentration exceeds a critical value. The aggregates can be gathered and mechanically spun into macroscopic fibers according to the method of O'Brien et al. [L O'Brien et al., "Design, Synthesis and Fabrication of Novel Self-Assembling Fibrillar Proteins", in *Silk Polymers: Materials Science and Biotechnology*, pp. 104–117, Kaplan, Adams, Farmer and Viney, eds., c. 1994 by American Chemical Society, Washington, D.C.].

The following examples are provided to illustrate the invention in more detail. The examples are not to be taken as limiting the invention, the scope of which is rather defined by the claims following.

EXAMPLE I cDNA Clones Encoding Minor Ampullate Silk Proteins

The minor ampullate glands are small, J-shaped organs located in the abdomen of the spider. The minor ampullate glands (about 20) were removed from a number of spiders and frozen in liquid nitrogen. Total RNA was prepared from the frozen tissue by standard methods. cDNA was prepared from the total RNA using the RIBOCLONE™ system (Promega). The synthesis method was modified slightly by using pseudorandom hexamers in addition to the Noti primer-adapter in the primer extension steps. The pseudo-random hexamers were synthesized having the sequence (A or T)(G or C)(G or C)(A or T)(G or C)(G or C). Such hexamers reflect the sequence bias in the minor ampullate silk proteins (minor spidroins, MiSP) we hypothesized would be imposed by repetition of alanine and glycine residues, which are found in large proportion in the amino acid composition of solubilized minor ampullate silk. We anticipated that so biasing the primer composition would enrich the library in long cDNAs encoding MiSP proteins.

The cDNA thus synthesized was ligated to appropriately digested pGEM3Zf(−) plasmid (Promega) and the ligation mixture was used to transform SURE™ *E. coli* cells (Stratagene). Plasmid DNA was prepared from randomly selected transformed colonies and the insert DNA was partially sequenced, using the forward and reverse primers provided by the supplier (Promega), that are complementary to the vector sequence near the insert. Clones having inserts encoding highly repetitive sequences were examined in greater detail with respect to insert size. Clones having an insert size greater than 1.5 kbp were sequenced in their entirety.

The entire insert of the pMISS1 (encoding MiSP1) has been sequenced. The nucleotide sequence and the resulting translation are shown in FIGS. 1A–1F. A restriction map is shown as FIG. 5. The region from nucleotides 96–137 is represented as indeterminate. That portion of the cDNA is found to have a much higher GC content than the remainder of the sequence. As a result, that portion of the nucleotide sequence has not been resolved due to "compression" observed in the electrophoresis step. pMISS1 contains an open reading frame beginning with the ATG start codon at nucleotides 183–185. The open reading frame encodes a 5'-nonrepetitive region, an indirect repetitive region and a 3'-nonrepetitive region. The 5'-nonrepetitive region contains a sequence of about 16 residues (amino acids 2–17) that conforms to secretion signal sequences. The presence of the leader peptide suggests that the MiSP1 protein is processed and secreted through the endoplasmic reticuium.

Table 1 shows the MiSP1 amino acid sequence formatted to show the 13 unit repeats (SEQ. ID. NOS.:19–31) of the MiSP1 protein.

SEQ. ID. NO.:34)

$(XGG)_w(XGA)(GXG)_x(AGA)_y(G)_zAG$ where X is tyrosine or glutamine
and where w=2–3, x=1–3, y=5–7, and z=1 or 2. SEQ. ID. NO.:35)

$(GPG_2YGPGQ_2)_a(X)_2S(A)_b$ where X=GPG or GPS
and where a=2 or 3 and b=7 to 10.

Inspection of the amino acid sequence of MiSP1 shows that, for the most part, the protein can be viewed as a derivatized polyamide. Accordingly, a polypeptide having the less complex generic formula: (SEQ. ID. No.:36):

$(GGX)_n(GA)_m(A)_l$ where X is tyrosine, glutamine or alanine and
where l=1 to 6, m=0 to 4 and n=1 to 4,
would also be expected to have many of the properties of the MiSP1 protein.

The 3'-nonrepetitive coding region of pMISS1 encodes a 96 amino acid spider silk consensus sequence that is 50% and 49% identical to the 3'-nonrepetitive regions of MaSP1 and MaSP2, respectively. The coding region ends at nucleotide position 2634 with a TAA stop codon. The 3' untranslated region of pMISS1 contains a poly(A) tail.

TABLE 1

Minor Ampullate Spidroin 1 Residues 92–706, showing alignment of unit repeats:

```
GAAGAGGYGRGAG- - - - - - - - - - - - - - - - GYGGQGGYGAGAGAGAAAAA
GAGAGGAGGYGRGAGAGAGAAAGAGAGAGGAGYGGQGGYGAGAGAGAAAAA
GAGAGGAGGYGRGAGAGAGAAAGAGA- - - - GGYGGQGGYGAGAGAGAAAAA
GAGSGGAGGYGRGAGAGAGAAAGAGAGA- - GS YGGQGGYGAGAGAGAAAAA
GAGAGGAGGYGRGAGAGAGAGAGAAARAGAGAGG- - - - - - - - - - - AAAAA
GAGAGGAGGYGRGAGAGAGAAAGAGAGA- - - - - GGYGGQSGYGAGAG- - AAAAA
GAGAGGAGGYGRGAGAGAGAAAGAGAAAGAGAGGYGGQGGYGAGAGAGAAAAA
GAGAGGAGGYGRGAGAGAGAAAGAGAG- - - - GYGGQGGYGAGAGAGAAAAA
- TGAGGAGGYGRGAGAGAGAAAGAGAGTGGAGYGGQGGYGAGAGAGAAAAA
GAGAGGGAG- YGRGAGAGAGAAAGAGAGAAAGAGAGGYGGQGGYGAGARAGAAAAA
GAGAGGAAGYS RGGRAGAAGAGAGAAAGAGAGAGGYGGQGGYGAGAGAGAAAAA
GAGSGGAGGYGRGAGAGAAAGAGAAAGAGAGAGGYGGQGGYGAGAGAGAAAAA
GAGAGRGGYGRGAGAGGYGGQGGYGAGAGAGAAAAA
```

- added for purposes of alignment

Each repeat is a variation of the consensus amino acid sequence (SEQ. ID. NO.:32) RGAAGAAGAGAGAAA-G A G A G A G A G G Y G G Q G G Y G - AGAGAGAAAAAGAGAGGAGGYG. This repetitive region can be described as a mixture of two types of units, (1) dimers of alanine separated by glycine residues, and (2) dimers of glycine separated by tyrosine or glutamine residues. It is thus distinguishable from the consensus sequence of the MaSP2 protein, which can be characterized as predominantly dimers of glycine or glutamine separated by proline or tyrosine residues.

Alternatively, the majority of the amino acid sequence of the MiSP1 protein can be described by a repeat unit having the generic (SEQ. ID. NO.:33)

Figure 6:
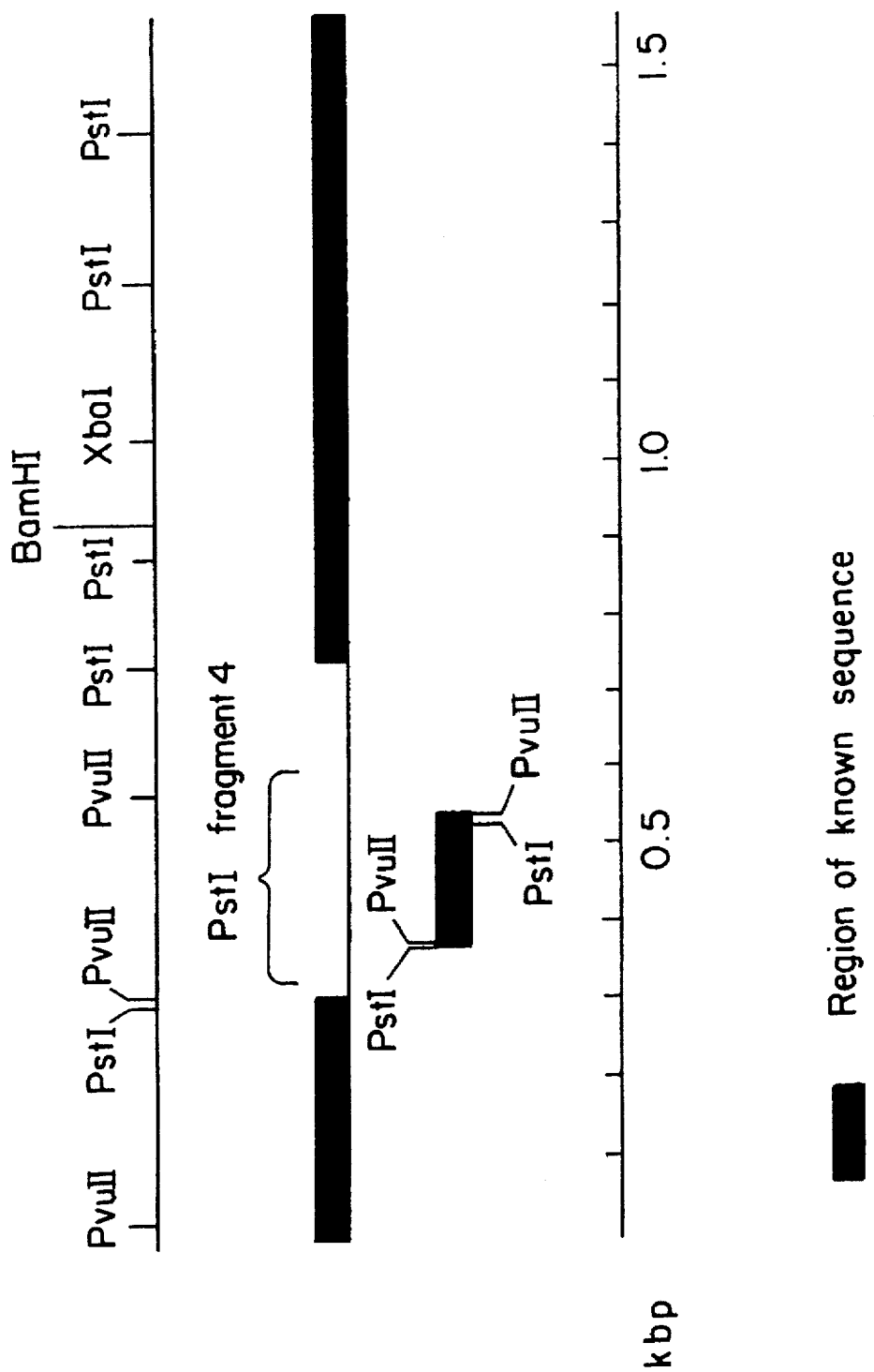
FIG. 6 shows a restriction map of the pMISS2 insert cDNA. Beneath the restriction map is a schematic showing the portions of the insert that have been sequenced.

$(GR)(GA)_l(A)_m(GGX)_n(GA)_l(A)_m$ where X is tyrosine, glutamine or alanine and
where l=1 to 6, m=0 to 4 and n=1 to 4. This finding is similar to what was observed for the MaSP1 and MaSP2 proteins, which exhibit the generic formulas:

The majority of the pMISS2 (encoding MiSP2) cDNA has been sequenced. The insert in pMISS2 is 1.6 kbp in length, of which 1344 nucleotides have been determined. The nucleotide sequence and translation of the completed portions of the DNA sequence are shown in FIGS. 2A–2D. FIG. 6 shows a restriction map of the pMISS2 clone and indicates what portions of the cDNA insert have been sequenced. pMISS2 contains an open reading frame beginning at the 5' end of the insert that does not begin with a methionine. This result strongly suggests that the pMISS2 cDNA lacks nucleotides encoding the amino terminus of the MiSP2 protein. The pMISS2 cDNA, like the pMISS1 cDNA encodes a 5'-nonrepetitive region, a repetitive region and a 3'-nonrepetitive region. The 5'- and 3'-nonrepetitive regions of MiSP1 and MiSP2 are aligned in FIG. 4. In contrast to MiSP1, the unit repeat that characterizes the repetitive region in MiSP2 is cryptic. As no clear unit repeat is yet distinguishable, no consensus repeat unit is yet derived. However, it is clear from inspection of the repetitive portion of MiSP2 that it is distinguishable from the repetitive portion of MiSP1.

Another pair of clones, designated 11-1 and 11-2, respectively (collectively pMISS3), are independent isolates of the same cDNA and are found to encode a third minor ampullate silk polypeptide (MiSP3). 11-1 contains a 2 kbp insert; 11-2 contains a 1.5 kbp insert. Partial nucleotide sequences have been obtained from both of these clones to date. The nucleotide sequences and translations thereof are presented as FIGS. 3A–3C.

Three different types of N-bromosuccinimide (NBS) peptides from minor ampullate silk have been purified. The first type of peptide has the amino acid sequence GGQGGY (SEQ. ID. NO.:56). The second type of peptides have a sequence encompassed by the generic formula $(GA)_n$, where n=3.5, 4.5, or 8.5. The third type of peptides have the sequence $(G)_n$, where n=6 or 9. The pMISS1, pMISS2, and pMISS3 clones all encode the GGQGGY (SEQ. ID. NO.:56) peptide and some variation of the $(GA)_n$ peptide. However, none of the isolated cDNAs, so far as they have been characterized to date, encode a $(G)_n$ peptide. Since pMISS1 has been completely sequenced, except for a small region of 42 nucleotides in a highly compressed region (high GC content) and does not contain the $(G)_n$ peptide, the minor ampullate silk must contain at least two proteins. Furthermore, while portions of the nonrepetitive regions of MiSP2 are identical to parts of the nonrepetitive regions MiSP1, the nonrepetitive regions of the two proteins are different. Also, the repetitive regions are different of MiSP1 and MiSP2 are distinguishable (see below). Although nonrepetitive portions have not yet been found in MiSP3, the repeats encoded by the 11-series isolates are distinguishable from the repeats of both MiSP1 and MiSP2 on two bases: (1) the spacing between Gln residues is only about one-half that seen in MiSP1 and MiSP2, and (2) Phe residues occasionally precede the GGQGGY (SEQ. ID. NO.:56) sequence whereas a Tyr always precedes the GGQGGY (SEQ. ID. NO.:56) sequence in MiSP1. Thus, the minor ampullate gland produces a silk comprised of at least three proteins.

EXAMPLE 2
Expression of a cDNA Encoding a Polypeptide Comprising the MaSP2 consensus sequence In order to demonstrate expression of an engineered spider silk protein, the consensus sequence from the MaSP2 protein (U.S. Ser. No. 07/684,819 was cloned into an *E. coli* expression vector. The consensus sequence was determined, using the considerations described above, from the alignment of the unit repeats of the MaSP2 protein. Table 2 shows the alignment of the unit repeats of the MaSP2 protein, (SEQ. ID. NO.:37–48).

The synthesis of the expression vector is described below and shown schematically in FIG. 7.

Two synthetic oligonucleotides were synthesized:
1) an 84 base oligonucleotide, named S21long (SEQ. ID. NO.:50)

5'-TCTAGCCCGGGTGGCTATGGTCCTGGA-
CAGCAAGGTCCTGGCGGTTACGGTCCTG-
GCCAACAGGGTCCCTCTGGTCCAGGCAGT-3'

2) a 59 base oligonucleotide, named S2short (SEQ. ID. NO.:51)

5'-TCCGGACCTGCTGCGGCGGCTGCG-
GCAGCTGCACTGCCTGGACCAGAGGGACCCTGTTG-3'

These oligonucleotides were designed to hybridize to each other in a 27 base region of complementarity, on the 3' end of each respective oligonucleotide. When the rest of the bases were filled in by VENT™ polymerase (New England Biolabs) and the product digested with Xma I (recognition site-CCCGGG), a double-stranded segment of DNA resulted which encoded the basic repetitive unit of MaSP2 (SEQ. ID. NO.:52, in single letter amino acid code):

PGGYGPGQQGPGGYGPGQQGPSGPGSAAAAAAAAG

The DNA segment, with an Xma I cut on the 5' end (with respect to the coding strand) and the other end blunt but containing a Bsp EI site, was ligated into pBLUESCRIPT™ II (Stratagene) which had been double digested with Xma I and Eco RV and agarose gel purified, thus giving a directional cloning with the inserted segment in frame with the lac I gene of pBLUESCRIPT™ II. It is important to note for the strategy explained later that Xma I and Bsp E I have compatible, nonregenerable overlaps. That is, DNA cut with these enzymes can be ligated, but the ligation will not regenerate either site. The ligated DNA was subjected to Eco RI digestion to reduce background (the Xma I, Eco RV digest of the vector eliminated the unique Eco RI site of pBLUESCRIPT™ II) and used to transform competent SURE™ *E. coli* cells (Stratagene).

Twelve white colonies (indicating inserts were present in the plasmid) resulted which were screened by digesting plasmid DNA obtained from the colonies (SCREENMAX™, J. T. Baker) with BssHII to release the insert. The insert sizes were determined by agarose gel electrophoresis.

Four colonies contained inserts of the predicted size. Plasmid DNA was prepared from those colonies by SCREENMAX™ and subjected to sequencing. One colony

TABLE 2

| Alignment of Unit Repeats of the MaSP2 Protein |
| --- |
| GP GQQGP GGYGP GQQGP - - S GP GS AAAAAAAAAA- - - - - GP GGYGP GQQGP GGY |
| GP GQQGP GRYGP GQQGP - - S GP GS AAAAAA- - - - - - - - - - - - - GS GQQGP GGY |
| GP RQQGP GGYGQGQQGP - - S GP GS AAAAS AAAS AES GQQGP GGYGP GQQGP GGY |
| GP GQQGP GGYGP GQQGP - - S GP GS AAAAAAAS - - - - - - - - - - - - GP GQQGP GGY |
| GP GQQGP GGYGP GQQGP - - S GP GS AAAAAAAAS - - - - - - - - - - - GP GQQGP GGY |
| GP GQQGP GGYGP GQQGL - - S GP GS AAAAAAAA- - - - - - - - - - - - - - - - - - - - - |
| GP GQQGP GGYGP GQQGP - - S GP GS AAAAAAAAA- - - - - - - - - - - - - - - - GP GGY |
| GP GQQGP GGYGP GQQGP - - S GAGS AAAAAAA- - - - - - - - - - - - - GP GQQGL GGY |
| GP GQQGP GGYGP GQQGP GGYGP GS AS AAAAAA- - - - - - - - - - - - - - - - - - - - - |
| GP GQQGP GGYGP GQQGP - - S GP GS AS AAAAAAAA- - - - - - - - - - - - - - - - GP GGY |
| GP GQQGP GGYAP GQQGP - - S GP GS AS AAAAAAAA- - - - - - - - - - - - - - - - GP GGY |
| GP GQQGP GGYAP GQQGP - - S GP GS AAAAAAAS A- - - - - - - - - - - - - - - - GP GGY | harbored a plasmid (hereafter referred to as pS2U) containing an insert that was usable, although its structure was not exactly as designed. The ninth base of S2short was changed to a G, most likely a result of a synthesis error, although the difference may also have been a mistake incorporated by the polymerase or a mutation occurring during the cloning manipulations. In addition, the first base of S2short is missing (or the first base of the Eco RV site, it is impossible to determine which). This could be due to nonspecific nuclease activity in restriction enzymes used to perform the recombinant DNA manipulations. However, these changes are not critical, since the G appears in a wobble position in the coding sequence, and the alteration of the blunt end ligation site may even have provided some advantages, putting several codons for arginine directly after the MiSP2 sequence.

Figure 7:
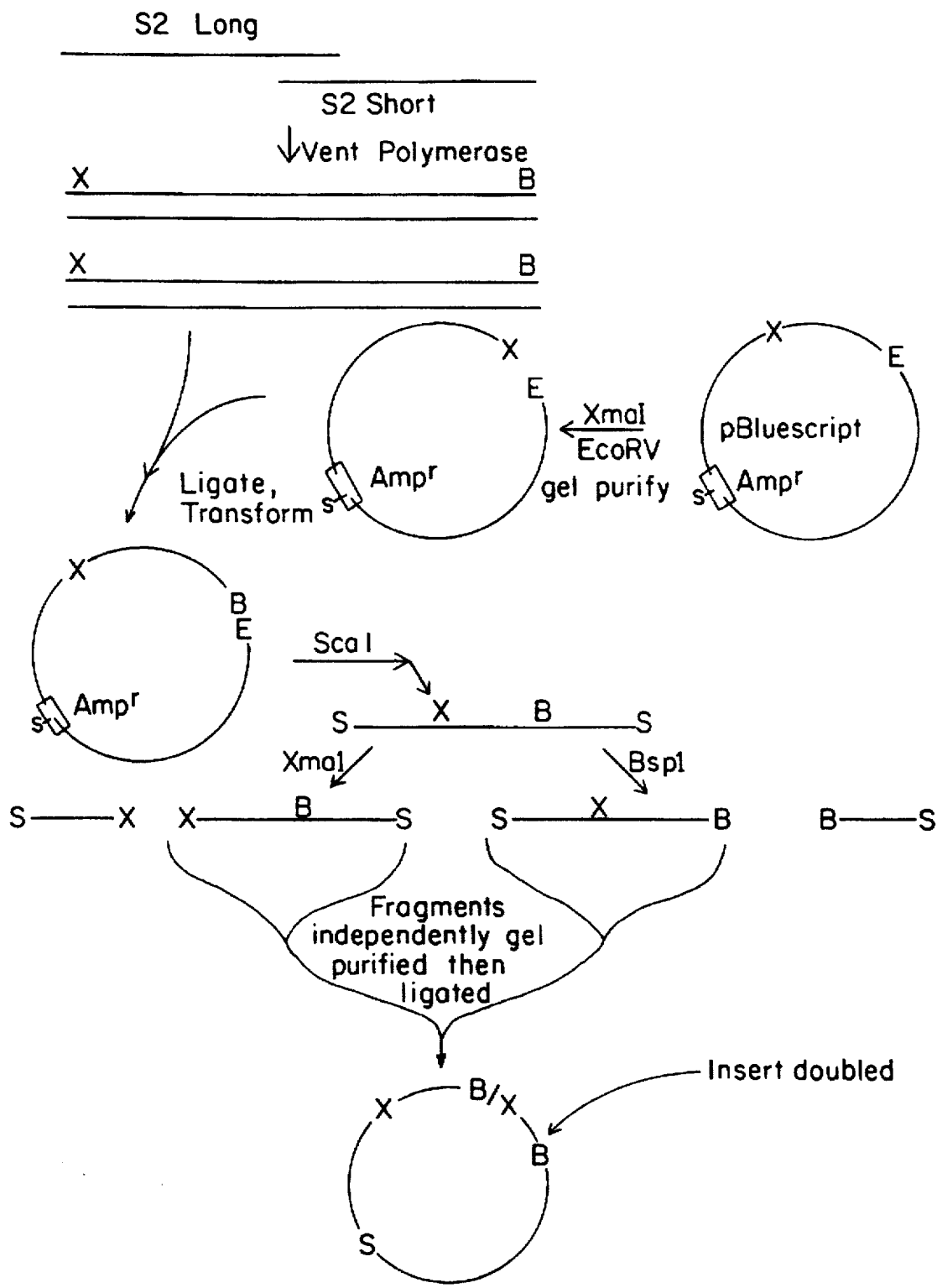
FIG. 7 shows a flow chart description of the synthesis of the pET19b-16 vector. Restriction sites are designated as: B, Bsp E1; E, Eco RV; S, Sca I; X, Xma I.

The insert was doubled, except for the additional arginine encoding codons, by manipulation of the restriction sites imbedded by design at the ends of the unit consensus sequence as well as a unique Sca I site in the ampicillin resistance gene of pBLUESCRIPT™ II (See FIG. 7). Plasmid from a miniprep is digested with Sca I, then divided into two aliquots. One aliquot is digested with Xma I and the other with Bsp E I. The digests are electrophoresed on 0.8% soft agarose, and the appropriate bands excised with a razor blade, and the DNA extracted using the standard procedure provided with β-agarase (New England Biolabs). The Sca I-Xma I segment containing one copy of the unit is then ligated to the Sca I-Bsp EI segment also containing one copy of the unit, thus effectively doubling the insert size while keeping both units in frame and regenerating the ampicillin resistance. This strategy can be repeated to derive any number of repeats of the unit desired (until secondary structure or insert size interferes). Thus an engineered vector encoding a polypeptide comprising 16 repeats of the MaSP2 consensus sequence was constructed in pBLUESCRIPT™ II.

The insert encoding 16 repeating units of the MaSP2 consensus sequence was placed in pET19b by cutting the HincII site of pBLUESCRIPT™ (creating a blunt end) then ligating a Bam H1 linker of the appropriate size to that end. The fragment was then subjected to Bam H1 cleavage, which cut at both ends, due to the presence of a Bam H1 site in pBLUESCRIPT™ a few bases 5' of the insert. This 5' Bam H1 site was engineered to be in frame with the Bam H1 insertion site of the pET system of vectors (Novagen). As noted below, the pET vector system allows affinity purification of expressed proteins using affinity recognition of a polyhistidine leader sequence attached to the desired protein. The insert was agarose gel purified, ligated into Bam H1-cut, phosphatased pET19b and the result used to transform competent SURE™ E. coli (Stratagene). The resultant colonies were screened and the orientation of the inserts determined by restriction digest. Clones with properly oriented inserts were then used for expression experiments.

BL31 DE3 E. coli (Novagen) were transformed with a plasmid having the insert in the desired orientation (pET19b-16) and plated on LB agarose plates containing chloramphenicol and carbenicillin. Antibiotic resistant colonies were picked an grown in LB medium containing chloramphenicol and carbenicillin to an $OD_{600}$ of about 0.8. One mL of the resulting inoculum was saved as a freezer stock. inoculum cultures should be grown to $OD_{600}$ of 0.8 or less, in order to maintain antibiotic selection pressure.

Five mL of the inoculum was used to inoculate 50 mL of LB containing the antibiotics. When the OD600 reached 0.8, the cells were collected by centrifugation and resuspended in 50 mL of fresh medium. The resuspended culture was diluted into 500 mL of LB containing the antibiotices and culture was continued until the $OD_{600}$ reached 0.8. IPTG was added to a concentration of 0.8 mM to initiate expression of the synthetic spider silk gene.

After four hours, the cells were collected by centrifugation and resuspended in a lysis buffer modified from the method of Sambrook et al. (50 mM Tris-Cl (pH 8.0), 10 mM $MgCl_2$, 100 mM NaCl), and lysed with lysozyme in the presence of PMSF according to Sambrook et al. [j. Sambrook et al., *Molecular Cloning: A Laboratory Manual*, 2nd ed., pp. 17.23–17.44, c. 1989 by Cold Spring Harbor Laboratory Press, Cold Spring Harbor, N.Y.].

The MaSP2 consensus polypeptide was purified from the lysate by affinity purification using a $Ni^{2+}$ column, as described by the technical manual provided by the manufacturer (Novagen). The divalent metal complexes the polyhistidine leader sequence encoded by the pET vector. A single step affinity purification provided the desired fusion protein at 95% purity.

Figure 8A:
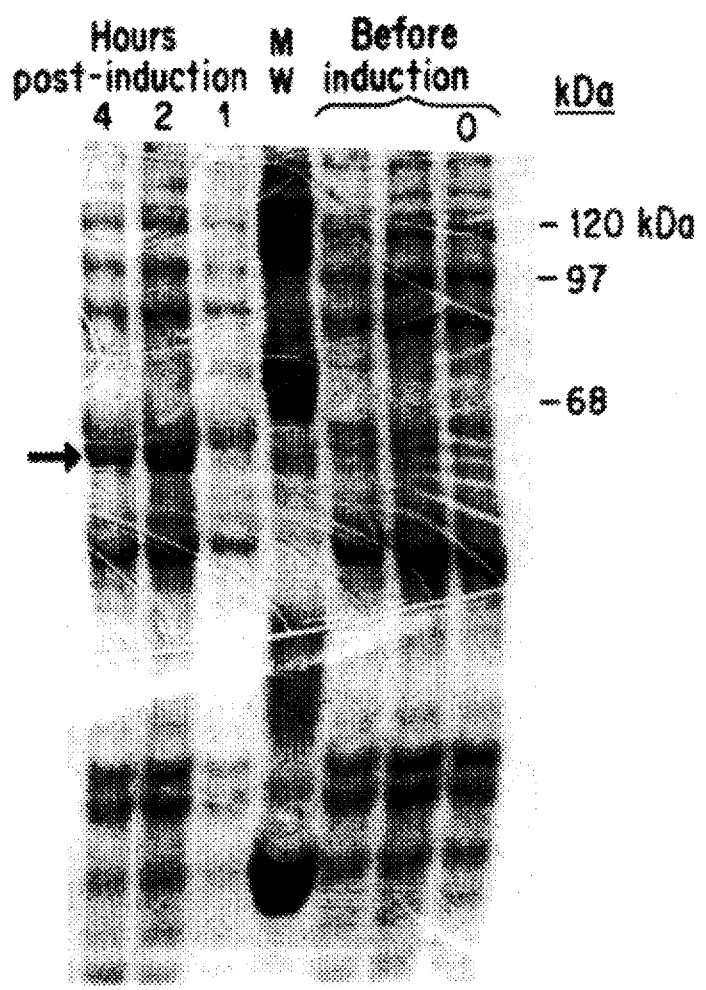
FIGS. 8A–8B shows analysis of the purification of a synthetic spider silk protein expressed from the pET19b-16 vector. 8A shows analysis of the crude lysate at 1, 2 and 4 hours post-induction. 8B shows analysis of the protein purified by $Ni^{2+}$ affinity purification.
Figure 8B:
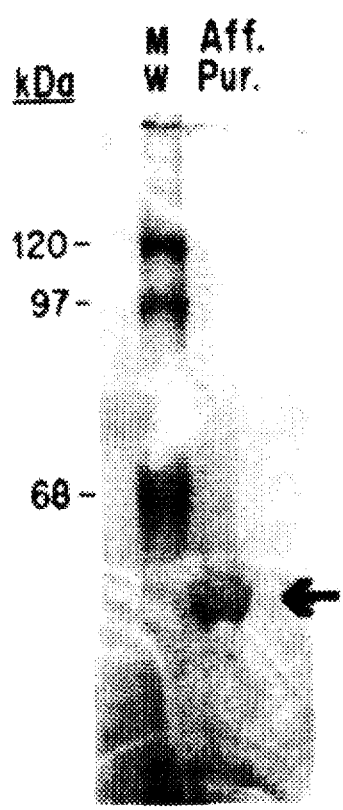

For cleavage of the polyhistidine leader peptide, the eluant from the affinity column was dialysed against distilled water for 24 hours to remove salts. The solution was made to 25 mM in ammonium bicarbonate and TPCK-treated trypsin was added to 1/20 the amount of the protein content of the eluate by weight. The digestion reaction was incubated at 37° C. for 4 hours. An additional aliquot of trypsin was added and the incubation was continued for an additional 4 hours. The leader peptide fragment was separated from the synthetic spider silk polypeptide by gel filtration chromatography on SEPHADEX™ G-50. FIG. 8 shows the results obtained using the above-described system. Approximately 10 mg of the MiSP2 consensus polypeptide are obtained from a 500 mL culture. The molecular weight of 58 kDa is the expected molecular weight for the polypeptide having a sequence of 16 repeats of the MiSP2 consensus sequence.

EXAMPLE 3

A Generalized Method for Preparing Vectors for Expression of Spider Silk Protein Consensus Polypeptides Following is a general method for generating artificial genes for any repetitive protein that contains polyalanine stretches. The method can thus be applied to express a protein comprising the consensus polypeptide of any of the major or minor ampullate spidroin proteins described herein.

The method employs two particular restriction enzymes, Sfi I and AlwN I (recognition sites shown below):

Sfi I: GGCCNNNN/NGGCC (SEQ. ID NO.:53) AlwN I: CAGNNN/CTG

An oligomer is designed such that a Bam HI site is in frame with and immediately precedes an Sfi I site. The Bam H I site will also be in frame with the pET system of vectors which are used for expression. However, the manipulations which are needed to produce multiple copies of the artificial unit will not involve this site, since it is 5' to the Sfi I site. Sfi I and AlwN I are used as the primary enzymes for manipulations for unit multiplication because the recognition sequences of both of these enzymes can (1) code for polyalanine stretches (see below) and (2) can form a pair of compatible, nonregenerable sites.

Ala Ala Ala Ala (SEQ. ID. NO.:53) Ala Ala Ala

Sfi I: G/GCC/GCA/GCG/GCC (SEQ. ID. NO.:54) AlwN I: GCA/GCA/GCT

Two oligonucleotides are designed that will reverse complement each other on their 3' ends, allowing hybridization. The first contains the Bam HI site, followed (in frame) by the Sfi I site representing the polyalanine region of MiSP1, followed by DNA encoding approximately two-thirds of the repetitive portion of MiSP1. The second oligonucleotide will be the anti-coding strand of MiSP1, starting with an AlwN I site and encoding approximately two-thirds of the repetitive region.

The simple diagram below shows the intended overlap of the the oligonucleotides and the placement of the restriction enzymes sites.

After hybridization, the overhanging ends are filled with VENT™ polymerase. The resultant double-stranded product is digested with Bam H I and, after agarose gel purification, cloned into a Bam H I cut, Eco R V cut pBLUESCRIPT™ II vector. This ligation mixture is digested with Eco R I (to reduce background) and used to transform competent SURE™ E. coli cells. Plasmid DNA is prepared from resulting colonies and screened first for insert size, then sequenced to determine if the insert is properly integrated.

To double the insert to appropriate size, double digests with Sca I (found in the Amp$^r$ gene of BLUESCRIPT™) and either Sfi I or AlwN I are performed and the resultant fragments gel purified. The 5' Sca I-Sfi I-AlwN I 3' fragment of the Sca I+AlwN I digest is ligated to the 5' Sfi I-AlwN I-Sca I 3' fragment from the Sca I+Sfi I digest. This will regenerate a functional pBLUESCRIPT™ II which will include a doubled artificial gene. Since Sfi I and AlwN I ends are compatible they will ligate, but the resulting splice site will not regenerate a recognition site for either enzyme. This allows the doubling to be extended to 4-, 8-, 16-, and higher multimers of the original insert.

The final vector+multimer can then be cut with Hinc II, ligated with Bam H I linkers of an appropriate length, cut with Bam H I to liberate the insert, and cloned directly into the pET system of vectors for expression.

EXAMPLE 4
Optimization of Expression of DNA Encoding Spider Silk Proteins

In order to increase the yield of spider silk proteins expressed from cloned DNA in bacteria, the above-described culture methods can be modified. In particular, due to the large proportion of glycine, alanine, glutamine and proline in the proteins, supplementation of the culture medium used to grow cells for expression with these amino acids is expected to allow increased yield of the spider silk protein. Also, the culture density can be increased by use of high-density fermentation methods standard in the art [See, e.g. Reisenburg et al., Applied Microbiology and Biotechnology 34:77 (1990); Alberghina et al., Applied Microbiology and Biotechnology 34:82 (1990)]. For instance, increasing the $OD_{600}$ at which expression is initiated from 0.8 to 20 would be expected to produce a concomittant increase in yield from 20 mg/L to 480 mg/L.

The vector used to support replication of the cloned DNA and to drive its expression can also be changed. The basic pET system described above is available from the supplier (Novagen) in many variations. One characteristic which makes the pET system advantageous is that expression of inserts in the pET vectors is very tightly regulated. Very little of the cloned DNA is expressed until transcription of the insert DNA is induced. When transcription is induced, additional elements of the pET vector inhibit production of host cell proteins, thereby putting most of the protein synthetic resources of the cell to work to make protein encoded by the insert DNA.

However, the use of chloramphenicol and carbenicillin resistance to provide selection pressure is disadvantageous for high-level expression of proteins. Accordingly, use of a different antibiotic selection, e.g. kanamycin resistance, is expected to provide increased yields of protein by expression of DNA cloned in pET vectors.

Another advantage of the system used in the present case is that the polyhistidine leader peptide provides an affinity purification method that can be used even in the presence of chaotropic agents. This would allow purification of spider silk proteins fused to such a polyhistidine sequence which might be made in "inclusion bodies", aggregates of insoluble protein, that require harsh solubilization procedures prior to purification.

The host cell strain used for expression can also be optimized. Cells having a high level of tRNA for Ala, Gln, Gly and Pro codons could be made and used for expression of spider silk proteins. Also, the cellular protease complement of the cells can be manipulated to minimize degradation of the expressed protein.

It is considered that the spider silk proteins of the present invention can be expressed in appropriately engineered insect cells, using commonly available baculovirus vectors.

EXAMPLE 5
Preparation of Fibers From Spider Silk Proteins

As noted above, the spider silk proteins can be viewed as derivatized polyamides. Accordingly, the methods for producing fiber from soluble spider silk proteins is similar to that used to produce typical polyamide fibers, e.g. nylons, and the like.

O'Brien et al. [supra] describe fiber production from adenovirus fiber proteins. In a typical fiber production, the spider silk proteins are solubilized in a strongly polar solvent. The protein solution is typically greater than 5% in protein concentration. The solution is preferably between 8 and 20% in protein.

Fibers are preferably spun from solutions demonstrating properties indicating a liquid crystal phase. The concentration at which the phase transition will occur is different for particular polypeptide compositions. However, the phase transition can be monitored by observing the clarity and birefrigence of the solution. Onset of the a liquid crystal phase is detected by a translucent appearance of the solution and the observation of birefringence when the solution is viewed through crossed polarizing filters.

The solvent used to dissolve the spider silk protein is preferably highly polar. Such solvents are exemplified by di- and tri-haloacetic acids, haloalcohols (e.g. hexafluoroisopropanol). In some instances, co-solvents such as acetone are useful. Also, solutions of chaotropic agents, such as lithium thiocyanate, guanadine thiocyanate or urea can be used.

In one fiber-forming technique, fibers are first extruded from the protein solution through an orifice into methanol, until a length sufficient to be picked up by a mechanical means is produced. Then the fiber is pulled by such mechanical means through the methanol solution, collected and dried. The methods for drawing fibers are considered well-known in the art. Fibers made from the 58 kDa synthetic MaSP consensus polypeptide, described in Example 2, for instance, can be drawn by methods similar to those used for drawing low molecular weight nylons.

The invention being thus described, various modifications of the materials and methods disclosed herein will be apparent to one of skill in the art. Such modifications are to be considered encompassed by the scope of the invention described by the claims below. Articles of the scientific and patent literature cited herein are incorporated by reference in their entirety by such citation.

---

What is claimed is:

1. An isolated DNA molecule encoding a polypeptide having an amino acid sequence comprising repeats of the unit amino acid sequence of SEQ. I.D. NO. 32.

2. An isolated DNA molecule having the nucleotide sequence of SEQ. ID. NO. 1.

3. A host cell transformed with a DNA according to claim 1.

4. A host cell transformed with a DNA according to claim 2.

5. An isolated DNA molecule encoding a polypeptide comprising repeats of an amino acid sequence having the generic formula $(GR)_l(GA)_m(A)_n(GGX)_n(GA)_l(A)_m$ where X is tyrosine, glutamine or alanine and where l=1 to 6, m=0 to 4 and n=1 to 4.

6. A host cell transformed with a DNA molecule according to claim 5.

7. An isolated DNA molecule encoding a polypeptide comprising direct repeats of an amino acid sequence having the generic formula:

$(GGX)_n(GA)_m(A)_l$ where X is tyrosine, glutamine or alanine and where l=1 to 6, m=0 to 4 and n=1 to 4.

8. A host cell transformed with a DNA molecule according to claim 7.

9. An isolated DNA molecule comprising a polynucleotide that will hybridize to a DNA molecule having the sequence of SEQ. I.D. NO. 1 under conditions obtained by a solution of 6× SSC or SSPE, 5× Denhardt's solution, 0.5% SDS at a temperature of about 68° C., or under conditions obtained by the said solution that is made 50% in formamide at a temperature of about 42° C.

10. An isolated DNA molecule encoding a polypeptide comprising a plurality of units of amino acid sequences selected from the group consisting of the amino acid sequences of SEQ. I.D. NO. 19, SEQ. I.D. NO. 20, SEQ. I.D. NO. 21, SEQ. I.D. NO. 22, SEQ. I.D. NO. 23, SEQ. I.D. NO. 24, SEQ. I.D. NO. 25, SEQ. I.D. NO. 26, SEQ. I.D. NO. 27, SEQ. I.D. NO. 28, SEQ. I.D. NO. 29, SEQ. I.D. NO. 30, and SEQ. I.D. NO. 31.

11. An isolated DNA molecule comprising an isolated DNA molecule according to claim 10 and further comprising a nucleotide sequence encoding the amino acid sequence of SEQ. I.D. NO. 15 ligated to the 5' end of the nucleotide sequence according to claim 10.

12. An isolated DNA molecule comprising an isolated DNA molecule according to claim 10 and further comprising a nucleotide sequence encoding the amino acid sequence of SEQ. I.D. NO. 17 ligated to the 3' end of the nucleotide sequence according to claim 10.

13. An isolated DNA molecule comprising an isolated DNA molecule according to claim 12 and further comprising a nucleotide sequence encoding the amino acid sequence of SEQ. I.D. NO. 15 ligated to the 5' end of the nucleotide sequence according to claim 12.

14. An isolated DNA molecule according to claim 10, wherein all of the units are the same.

15. An isolated DNA molecule comprising a nucleotide sequence according to SEQ. I.D. NO. 5 or a plurality of repeats of said nucleotide sequence.

16. An isolated DNA molecule comprising an isolated DNA molecule according to claim 15 and further comprising a nucleotide sequence according to SEQ. I.D. NO. 7 ligated to the 3' end of said nucleotide sequence according to claim 15.

17. An isolated DNA molecule comprising an isolated DNA molecule according to claim 16 and further comprising a nucleotide sequence according to SEQ. ID. NO. 3 ligated to the 5' end of said nucleotide sequence according to claim 16.

18. An isolated DNA molecule comprising an isolated DNA molecule according to claim 15 and further comprising a nucleotide sequence according to SEQ. I.D. NO. 3 ligated to the 5' end of said nucleotide sequence according to claim 15.

19. An isolated DNA molecule comprising a plurality of units of nucleotide sequences selected from the group consisting of the nucleotide sequences of SEQ. I.D. NO: 9, SEQ. I.D. NO: 11 and SEQ. I.D. NO:13.

* * * * *